US012797870B2

United States Patent
(12) United States Patent
Takasuna et al.

(10) Patent No.: US 12,797,870 B2
(45) Date of Patent: Nov. 17, 2026

(54) DROPLET JET DEVICE

(71) Applicant: SEIKO EPSON CORPORATION, Tokyo (JP)

(72) Inventors: Shoichi Takasuna, Shiojiri (JP); Hirokazu Sekino, Chino (JP)

(73) Assignee: SEIKO EPSON CORPORATION (JP)

(*) Notice: Subject to any disclaimer, the term of this patent is extended or adjusted under 35 U.S.C. 154(b) by 507 days.

(21) Appl. No.: 17/972,694

(22) Filed: Oct. 25, 2022

(65) Prior Publication Data

US 2023/0128464 A1 Apr. 27, 2023

(30) Foreign Application Priority Data

Oct. 26, 2021 (JP) ................................ 2021-174419

(51) Int. Cl.
*B05B 1/08* (2006.01)
*A61B 17/3203* (2006.01)

(52) U.S. Cl.
CPC ............ *B05B 1/08* (2013.01); *A61B 17/3203* (2013.01)

(58) Field of Classification Search
CPC .. B05B 1/02; B05B 1/046; B05B 1/08; A61B 17/3203; A61B 2017/32032; A61B 2017/32035
USPC .................. 239/101, 601, 452, 597, 600, 99
See application file for complete search history.

(56) References Cited

U.S. PATENT DOCUMENTS 4,925,106 A 5/1990 Maas et al.
2008/0211871 A1 9/2008 Sakurai et al.
2010/0111708 A1* 5/2010 Seto .................. A61B 17/3203 417/44.1
2010/0243753 A1* 9/2010 Doak .................... B05B 7/0475 239/398
2012/0181352 A1* 7/2012 Seto ........................ F04B 43/08 239/101

FOREIGN PATENT DOCUMENTS

CN 101284447 A 10/2008
JP H04-500038 A 1/1992
JP 2021-023998 A 2/2021

* cited by examiner

*Primary Examiner* — Arthur O. Hall
*Assistant Examiner* — Juan C Barrera
(74) *Attorney, Agent, or Firm* — Harness, Dickey & Pierce, P.L.C.

(57) ABSTRACT

A droplet jet device configured to form a liquid into droplets to jet the droplets, the droplet jet device including a main body having a flow channel through which the liquid circulates, and a jet nozzle having at least one nozzle hole and spraying the liquid from the nozzle hole, wherein defining the number of the nozzle holes as N, a diameter of the nozzle hole as r [m], and a contour length of a cross-sectional surface of the flow channel as L [m], the following formula is fulfilled.

$$0.188 < \frac{1}{N^2} \cdot \frac{L^2}{r^3} < 1.58 \times 10^{16}$$

6 Claims, 10 Drawing Sheets

DROPLET JET DEVICE

The present application is based on, and claims priority from JP Application Serial Number 2021-174419, filed Oct. 26, 2021, the disclosure of which is hereby incorporated by reference herein in its entirety.

BACKGROUND

1. Technical Field

The present disclosure relates to a droplet jet device.

2. Related Art

In the past, there have been used a variety of types of droplet jet device for spraying a liquid in a droplet state such as cleaning equipment or cosmetic equipment. For example, in JP-T-4-500038 (Document 1; the term "JP-T" as used herein means a published Japanese translation of a PCT patent application), there is disclosed a bubble nozzle structure which can eject a sprayed liquid by continuously forming bubbles.

In the droplet jet device for spraying the liquid in the droplet state, when being used in, for example, the cleaning equipment or the cosmetic equipment, there is performed crushing an object, cleaning a human skin, or the like by making the droplets collide with the object or the human skin. In such a case, it becomes necessary for the liquid to be sprayed as droplets with high rectilinearity from a jet nozzle of the droplet jet device. However, in the bubble nozzle structure disclosed in Document 1, the liquid having been sprayed is mixed with air to be foamed, and is ejected as the sprayed liquid. In the configuration in which the liquid is ejected as the sprayed liquid, in some cases, it is unachievable to spray the liquid as droplets with high rectilinearity, which cannot be said that the liquid is sprayed in a preferable droplet state.

SUMMARY

In view of the problems described above, a droplet jet device according to the present disclosure is a droplet jet device configured to form a liquid into droplets to jet the droplets, the droplet jet device including a main body having a flow channel through which the liquid circulates, and a jet nozzle having at least one nozzle hole, in which $$0.188 < \frac{1}{N^2} \cdot \frac{L^2}{r^3} < 1.58 \times 10^{16}$$

in which N is a number of the nozzle holes, r [m] is a diameter of the nozzle hole, and L [m] is a contour length of a cross-sectional surface of the flow channel having contact with the liquid.

In view of the problems described above, another droplet jet device according to the present disclosure is a droplet jet device configured to form a liquid into droplets to jet the droplets, the droplet jet device including a main body having a flow channel through which the liquid circulates, and a jet nozzle having at least one nozzle hole, in which the flow channel has a circular cross-sectional shape, and $$1.90 \times 10^{-2} < \frac{1}{N^2} \cdot \frac{R^2}{r^3} < 1.60 \times 10^{15}$$

in which N is a number of the nozzle holes, r [m] is a diameter of the nozzle hole, and R [m] is a diameter of the flow channel.

In view of the problems described above, still another droplet jet device according to the present disclosure is a droplet jet device configured to form a liquid into droplets to jet the droplets, the droplet jet device including a main body having a flow channel through which the liquid circulates, and a jet nozzle having at least one nozzle hole, wherein the flow channel has a rectangular cross-sectional shape, and $$4.69 \times 10^{-2} < \frac{1}{N^2} \cdot \frac{(a+b)^2}{r^3} < 3.95 \times 10^{15}$$

in which N is a number of the nozzle holes, r is a diameter of the nozzle hole, a is a length of one side of the cross-sectional shape of the flow channel, and b is a length of another side of the cross-sectional shape of the flow channel.

DESCRIPTION OF AN EXEMPLARY EMBODIMENT

Figure 1:
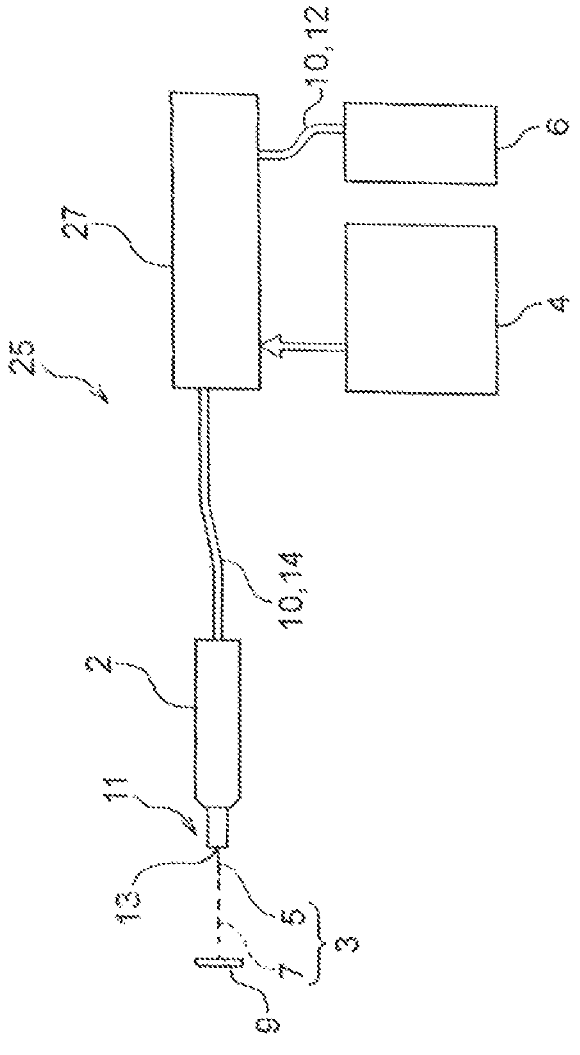
FIG. 1 is an overall schematic configuration diagram of a droplet jet device according to an embodiment of the present disclosure.

First, the present disclosure will hereinafter be described schematically.

In order to solve the problem described above, a droplet jet device according to a first aspect related to the present disclosure is a droplet jet device for forming droplets of a liquid and then discharging the droplets, and is characterized by including a main body having a flow channel through which the liquid circulates, and a jet nozzle having at least one nozzle hole, wherein the following formula is fulfilled when defining the number of the nozzle holes as N, a diameter of the nozzle hole as r [m], and a contour length of the cross-sectional surface of the flow channel making contact with the liquid as L [m].

$$0.188 < \frac{1}{N^2} \cdot \frac{L^2}{r^3} < 1.58 \times 10^{16}$$

According to the present aspect, the number of the nozzle holes, the diameter of the nozzle holes, and the contour length of the cross-sectional surface of the flow channel are determined so as to fulfill the formula described above. By adopting the droplet jet device determined as described above, it is possible to spray the liquid in a preferable droplet state irrespective of the cross-sectional shape of the flow channel.

The droplet jet device according to a second aspect is characterized in that the diameter of the nozzle hole is in a range no smaller than 100 μm and no larger than 1 mm, and fulfills the following formula in the first aspect.

$$1.53\times10^{7}N<L<1.41\times10^{3}N$$

According to the present aspect, when the diameter of the nozzle hole is in a range no smaller than 100 μm and no larger than 1 mm, it is possible to spray the liquid in the preferable droplet state irrespective of the cross-sectional shape of the flow channel using almost all liquids to be used generally.

The droplet jet device according to a third aspect is characterized in that the diameter of the nozzle hole is in a range no smaller than 1 μm and no larger than 100 μm, and fulfills the following formula in the first aspect.

$$4.34\times10^{-10}N<L<4.44\times10^{1}N$$

According to the present aspect, when the diameter of the nozzle hole is in a range no smaller than 1 μm and no larger than 100 μm, it is possible to spray the liquid in the preferable droplet state irrespective of the cross-sectional shape of the flow channel using almost all liquids to be used generally.

The droplet jet device according to a fourth aspect is characterized by fulfilling the following formula in the first aspect.

$$3.09\times10^{3} < \frac{1}{N^2}\cdot\frac{L^2}{r^3} < 2.66\times10^{13}$$

According to the present aspect, it is possible to spray the liquid in a preferable droplet state irrespective of the cross-sectional shape of the flow channel using almost all liquids to be used generally.

The droplet jet device according to a fifth aspect is characterized in that the diameter of the nozzle hole is in a range no smaller than 100 μm and no larger than 1 mm, and fulfills the following formula in the fourth aspect.

$$1.97\times10^{-5}N<L<5.77\times10^{1}$$

According to the present aspect, when the diameter of the nozzle hole is in a range no smaller than 100 μm and no larger than 1 mm, it is possible to spray the liquid in the preferable droplet state irrespective of the cross-sectional shape of the flow channel using almost all liquids to be used generally in cleaning equipment, cosmetic equipment, and so on.

The droplet jet device according to a sixth aspect is a droplet jet device characterized in that the diameter of the nozzle hole is in a range no smaller than 1 μm and no larger than 100 μm, and fulfills the following formula in the fourth aspect.

$$5.56\times10^{-8}N<L<1.82$$

According to the present aspect, when the diameter of the nozzle hole is in a range no smaller than 1 μm and no larger than 100 μm, it is possible to spray the liquid in the preferable droplet state irrespective of the cross-sectional shape of the flow channel using almost all liquids to be used generally in cleaning equipment, cosmetic equipment, and so on.

The droplet jet device according to a seventh aspect is characterized by fulfilling the following formula in the fourth aspect.

$$2.77\times10^{8} < \frac{1}{N^2}\cdot\frac{L^2}{r^3} < 9.24\times10^{11}$$

According to the present aspect, it is possible to spray the liquid in a preferable droplet state irrespective of the cross-sectional shape of the flow channel using water in a temperature range no lower than 20 °C and no higher than 40 °C or a liquid similar in characteristic to that water.

The droplet jet device according to an eighth aspect is characterized in that the diameter of the nozzle hole is in a range no smaller than 100 μm and no larger than 1 mm, and fulfills the following formula in the seventh aspect.

$$5.88\times10^{-3}N<L<1.07\times10^{1}N$$

According to the present aspect, when the diameter of the nozzle hole is in a range no smaller than 100 μm and no larger than 1 mm, it is possible to spray the liquid in the preferable droplet state irrespective of the cross-sectional shape of the flow channel using water in a temperature range no lower than 20 °C and no higher than 40 °C or a liquid similar in characteristic to that water.

The droplet jet device according to a ninth aspect is characterized in that the diameter of the nozzle hole is in a range no smaller than 100 μm and no larger than 1 mm, and fulfills the following formula defining a cross-sectional area of the flow channel as Ac [$m^2$] in the seventh aspect.

$$2.76\times10^{-6}N^2<A_c<9.19N^2$$

According to the present aspect, when the diameter of the nozzle hole is in a range no smaller than 100 μm and no larger than 1 mm, it is possible to spray the liquid in the preferable droplet state irrespective of the cross-sectional shape of the flow channel using water in a temperature range no lower than 20 °C and no higher than 40 °C or a liquid similar in characteristic to that water.

The droplet jet device according to a tenth aspect is characterized in that the diameter of the nozzle hole is in a range no smaller than 1 μm and no larger than 100 μm, and fulfills the following formula in the seventh aspect.

$$1.66\times10^{-5}N<L<3.40\times10{-}1N$$

According to the present aspect, when the diameter of the nozzle hole is in a range no smaller than 1 μm and no larger than 100 μm, it is possible to spray the liquid in the preferable droplet state irrespective of the cross-sectional shape of the flow channel using water in a temperature range no lower than 20 °C and no higher than 40 °C or a liquid similar in characteristic to that water.

The droplet jet device according to an eleventh aspect is characterized in that the diameter of the nozzle hole is in a range no smaller than 1 μm and no larger than 100 μm, and fulfills the following formula defining a cross-sectional area of the flow channel as Ac [$m^2$] in the seventh aspect.

$$2.20\times10^{-11}N^2<A_c<9.19\times10^{-3}N^2$$

According to the present aspect, when the diameter of the nozzle hole is in a range no smaller than 1 μm and no larger than 100 μm, it is possible to spray the liquid in the preferable droplet state irrespective of the cross-sectional shape of the flow channel using water in a temperature range no lower than 20 °C and no higher than 40 °C or a liquid similar in characteristic to that water.

The droplet jet device according to a twelfth aspect is a droplet jet device for forming droplets of the liquid and then discharging the droplets, and is characterized by including the main body having the flow channel through which the liquid circulates, and the jet nozzle having at least one nozzle hole, wherein the following formula is fulfilled when assuming the cross-sectional shape of the flow channel as a circular shape, and defining the number of the nozzle holes as N, the diameter of the nozzle hole as r [m], and the diameter of the flow channel as R [m].

$$1.90\times10^{-2} < \frac{1}{N^2}\cdot\frac{R^2}{r^3} < 1.60\times10^{15}$$

According to the present aspect, when the cross-sectional shape of the flow channel is a circular shape, it is possible to spray the liquid in the preferable droplet state.

The droplet jet device according to a thirteenth aspect is characterized by fulfilling the following formula in the twelfth aspect.

$$3.13\times10^{2} < \frac{1}{N^2}\cdot\frac{R^2}{r^3} < 2.69\times10^{12}$$

According to the present aspect, it is possible to spray the liquid in the preferable droplet state using almost all liquids to be used generally when the cross-sectional shape of the flow channel is a circular shape.

The droplet jet device according to a fourteenth aspect is characterized by fulfilling the following formula in the thirteenth aspect.

$$2.81\times10^{7} < \frac{1}{N^2}\cdot\frac{R^2}{r^3} < 9.36\times10^{10}$$

According to the present aspect, it is possible to spray the liquid in the preferable droplet state using water in a temperature range no lower than 20 °C and no higher than 40 °C or a liquid similar in characteristic to that water when the cross-sectional shape of the flow channel is a circular shape.

The droplet jet device according to a fifteenth aspect is characterized by fulfilling the following formula when the diameter of the nozzle hole is in a range no smaller than 1 μm and no larger than 100 μm in the thirteenth aspect.

$$5.30\times10^{-6}N < R < 1.08\times10^{-1}N$$

According to the present aspect, when the cross-sectional shape of the flow channel is a circular shape, and the diameter of the nozzle hole is in a range no smaller than 1 μm and no larger than 100 μm, it is possible to spray the liquid in the preferable droplet state using almost all liquids to be used generally.

The droplet jet device according to a sixteenth aspect is a droplet jet device for forming droplets of the liquid and then discharging the droplets, and is characterized by including the main body having the flow channel through which the liquid circulates, and the jet nozzle having at least one nozzle hole, wherein the following formula is fulfilled when assuming the cross-sectional shape of the flow channel as a rectangular shape, and defining the number of the nozzle holes as N, the diameter of the nozzle hole as r, a length of one side of the cross-sectional surface of the flow channel as a, a length of the other side of the cross-sectional surface of the flow channel as b.

$$4.69\times10^{-2} < \frac{1}{N^2}\cdot\frac{(a+b)^2}{r^3} < 3.95\times10^{15}$$

According to the present aspect, when the cross-sectional shape of the flow channel is a rectangular shape, it is possible to spray the liquid in the preferable droplet state.

The droplet jet device according to a seventeenth aspect is characterized by fulfilling the following formula in the sixteenth aspect.

$$7.73\times10^{2} < \frac{1}{N^2}\cdot\frac{(a+b)^2}{r^3} < 6.64\times10^{12}$$

According to the present aspect, it is possible to spray the liquid in the preferable droplet state using almost all liquids to be used generally when the cross-sectional shape of the flow channel is a rectangular shape.

The droplet jet device according to an eighteenth aspect is characterized by fulfilling the following formula in the seventeenth aspect.

$$2.77\times10^{7} < \frac{1}{N^2}\cdot\frac{(a+b)^2}{r^3} < 2.31\times13^{11}$$

According to the present aspect, it is possible to spray the liquid in the preferable droplet state using water in a temperature range no lower than 20 °C and no higher than 40 °C or a liquid similar in characteristic to that water when the cross-sectional shape of the flow channel is a rectangular shape.

The droplet jet device according to a nineteenth aspect is characterized by fulfilling the following formula assuming the cross-sectional shape is a square shape, and defining a length on a side of the square as p in the sixteenth aspect.

$$6.93\times10^{6} < \frac{1}{N^2}\cdot\frac{p^2}{r^3} < 5.78\times10^{10}$$

According to the present aspect, when the cross-sectional shape of the flow channel is a square shape, it is possible to spray the liquid in the preferable droplet state.

The droplet jet device according to a twentieth aspect is characterized in that the diameter of the nozzle hole is in a range no smaller than 1 μm and no larger than 100 μm, and fulfills the following formula defining a cross-sectional area of the flow channel as Ac [$m^2$] in the eighteenth or nineteenth aspect.

$$2.20\times10^{-11}N^2 < A_c < 7.22\times10^{-3}N^2$$

According to the present aspect, when the cross-sectional shape of the flow channel is a rectangular shape, and the diameter of the nozzle hole is in a range no smaller than 1 μm and no larger than 100 μm, it is possible to spray the liquid in the preferable droplet state using water in a temperature range no lower than 20 °C and no higher than 40 °C or a liquid similar in characteristic to that water. Alternatively, when the cross-sectional shape of the flow channel is a square shape, and the diameter of the nozzle hole is in a range no smaller than 1 μm and no larger than 100 μm, it is possible to spray the liquid in the preferable droplet state.

Embodiment of Droplet Jet Device

The droplet jet device 25 according to the embodiment of the present disclosure will hereinafter be described in detail based on FIG. 1. The droplet jet device 25 is a skin-cleaning droplet jet device suitable for cleaning of a skin of a face, an arm, a hand, a foot, a back, and so on. It should be noted that it is obvious that the droplet jet device 25 is not limited to those for skin cleaning.

As shown in FIG. 1, the droplet jet device 25 according to the present embodiment is provided with the jet nozzle 11 having at least one nozzle hole 13 for spraying the liquid 3, a pressurizing liquid supplier 27 for pressurizing the liquid 3 to feed the liquid 3 to the jet nozzle 11, and a controller 4 for controlling an operation of the pressurizing liquid supplier 27 to make the liquid 3 sprayed from the nozzle hole 13 fly toward an object 9 such as a skin in a state of being fragmented into droplets 7 from a continuous flow 5.

The droplet jet device 25 is provided with a spray unit 2 having the jet nozzle 11 for spraying the liquid 3, a liquid tank 6 for retaining the liquid 3 to be sprayed, a pump unit as the pressuring liquid supplier 27, a liquid suction tube 12 forming a flow channel 10 for the liquid 3 connecting the liquid tank 6 and the pressurizing liquid supplier 27 to each other, and a liquid sending tube 14 also forming the flow channel 10 connecting the pressurizing liquid supplier 27 and the spray unit 2 to each other. The pressurizing liquid supplier 27 is controlled by the controller 4 in a pump operation such as pressure of the liquid sent to the spray unit 2 through the liquid sending tube 14. In other words, the supply pressure is controlled. Here, the pressurizing liquid supplier 27 corresponds to the main body having the flow channel 10 through which the liquid 3 circulates.

It should be noted that the droplet jet device 25 is capable of spraying the liquid 3 from the spray unit 2 in a variety of conditions due to the control by the controller 4. A preferable configuration example of the droplet jet device 25 will hereinafter be described.

Two Conditions for Stable Droplet Jet

First, as a premise, there will be described two conditions for stable droplet jet. As described in "Journal of Jet Flow Engineering" Vol. 13, No. 1 (1996) pp. 86-98 and so on, it has been known that an aspect of a liquid jet flow jetted from a single nozzle hole 1 can be classified as follows using a jet number Je.

1. Dropping Region ($Je \leq 0.1$)
2. Smooth Flow Region ($0.1 < Je < 10$)
3. Wavy Flow Region ($10 \leq Je \leq 400$)
4. Spray Flow Region ($400 < Je$)

It has been known that it is necessary to spray the liquid 3 in the smooth flow region or the wavy flow region in order to stably form a droplet flow which is high in rectilinearity and small in variation in grain size from the liquid jet flow thus jetted. In other words, it is necessary to set parameters so as to fulfill $0.1 < Je \leq 400$. Here, the jet number Je is expressed as Formula (1) below. It should be noted that ρ represents a density [kg/m$^3$] of the liquid, σ represents a surface tension [N/m] of the liquid, v represents velocity [m/s] of the liquid, r represents a nozzle hole diameter [m], and ρa represents a density [kg/m$^3$] of air, respectively.

$$Je = \frac{\rho_a^{0.55} \cdot \rho^{0.45} \cdot rv^2}{\sigma} \tag{1}$$

Further, in order to make a lot of droplets 7 accurately hit home, it is necessary for the droplets 7 generated to have high rectilinearity. In the generation of the droplets 7 high in rectilinearity, it is indispensable for the liquid jet flow as a source of the droplets 7 to have the rectilinearity. In order to provide the liquid jet flow jetted from the nozzle hole 13 with the rectilinearity, it is necessary for the liquid 3 flowing through the flow channel 10 to be jetted in a laminar flow state from the nozzle hole 13. The aspect of a fluid flowing through the flow channel 10 such as a pipe is determined based on a value of the Reynolds number Re, and in general, when $Re \leq 2300$ is true, it is determined that the flow in the flow channel 10 is the laminar flow. Here, the Reynolds number Re is expressed as Formula (2) below. It should be noted that Q represents a volume flow rate [m$^3$/s], Ac represents a flow channel cross-sectional area [m$^2$], DH represents a hydraulic diameter [m], ν represents a kinematic viscosity coefficient [m$^2$/s], and ρ represents a viscosity coefficient [Pas], respectively.

$$\mathrm{Re} = \frac{QD_H}{vA_c} = \frac{\rho QD_H}{\mu A_c} \tag{2}$$

Control Example when Flow Channel has Circular Shape

Figure 2:
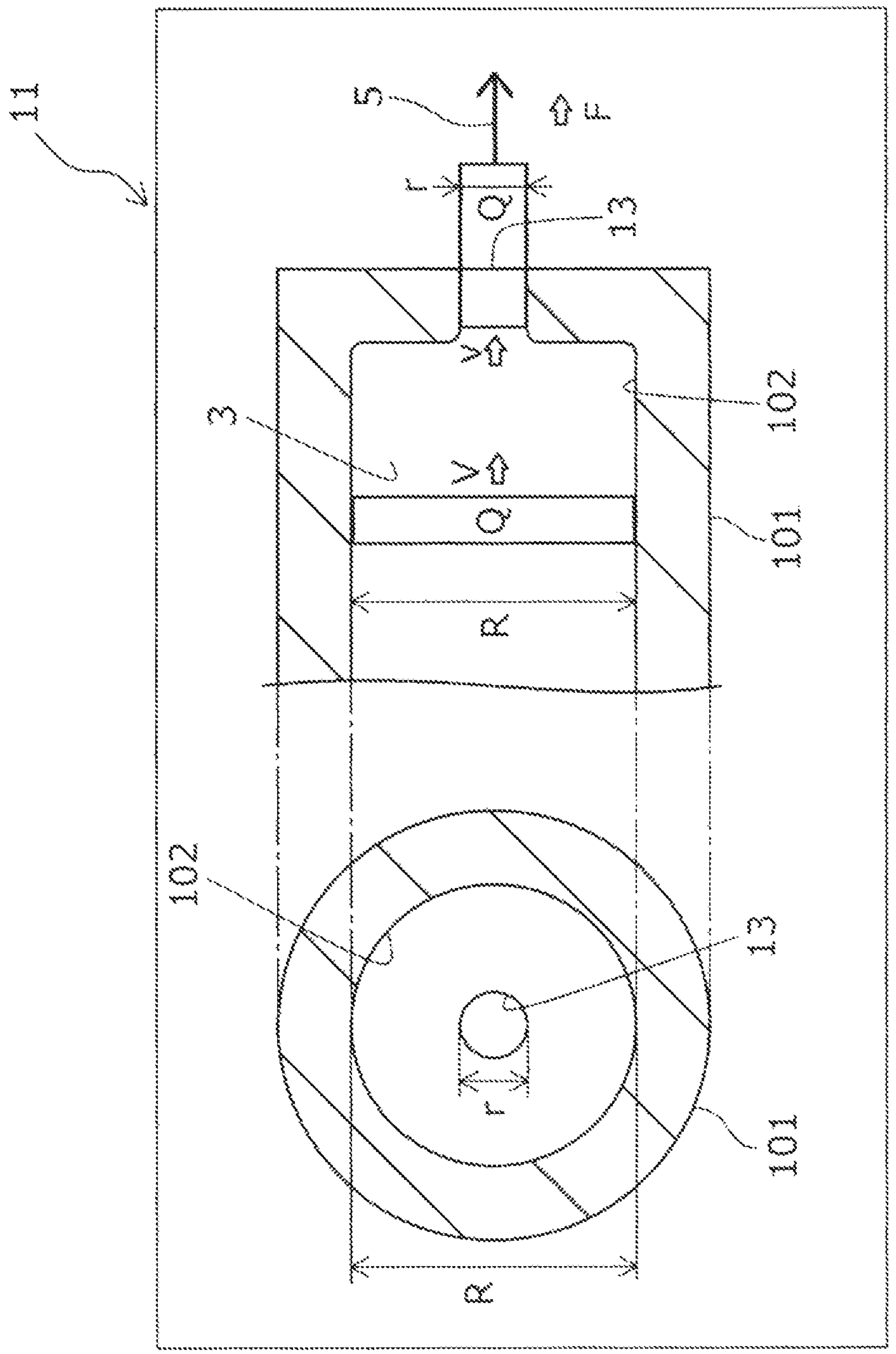
FIG. 2 is a schematic diagram of a jet nozzle when a cross-sectional shape of a flow channel is a circular shape.

There will be described a spray control example of the liquid 3 by the controller 4 when the shape of the flow channel 10 is a circular shape. Here, in FIG. 2, a left-hand diagram is a schematic diagram viewed from an ejection direction of the droplets 7, and a right-hand diagram is a side cross-sectional view corresponding to the left-hand diagram. In FIG. 2, the following parameters are schematically expressed so as to visually be recognized. It should be noted that the expression that the shape of the flow channel 10 is a circular shape means that the cross-sectional shape of the flow channel 10 in a portion adjacent to the jet nozzle 11 is a circular shape, and means that the cross-sectional shape of a flow channel inner wall 102 is a circular shape as shown in the left-hand diagram in FIG. 2. It should be noted that a shape of a flow channel outer wall 101 is not particularly limited.

When the flow channel 10 is a circular pipe, since the hydraulic diameter is equal to the diameter of the flow channel 10, when defining the flow channel diameter which is the diameter of the flow channel 10 as R [m], Formula (3) described below is obtained.

$$D_H = R \tag{3}$$

Here, by substituting Formula (3) in Formula (2), Formula (4) described below is obtained.

$$\mathrm{Re} = \frac{QR}{vA_c} = \frac{\rho QR}{\mu A_c} \tag{4}$$

Further, since an equation of continuity is true between the flow channel 10 and the nozzle hole 13, the volume flow rate Q fulfills Formula (5) described below. Here, V represents a flow velocity [m/s] in the flow channel 10, and A represents the total cross-sectional area [$m^2$] of the nozzle holes 13.

$$Q=A_cV=Av \tag{5}$$

Further, when a plurality of nozzle holes 13 the same in shape as each other is formed, the total cross-sectional area A of the nozzle holes 13 fulfills the relationship of Formula (6) described below. Here, N represents the number of the nozzles, and An represents the cross-sectional area [$m^2$] of each of the nozzle holes 13.

$$A=NA_n \tag{6}$$

Further, since the cross-sectional surface of the flow channel 10 and the cross-sectional surface of the nozzle hole 13 are each a circular shape, Ac and An are expressed as Formula (7) and Formula (8) described below using R and r.

$$A_c = \frac{\pi R^2}{4} \tag{7}$$

$$A_n = \frac{\pi r^2}{4} \tag{8}$$

Here, by substituting each of Formula (6) through Formula (8) in Formula (5), Formula (9) described below is obtained.

$$Q = \frac{\pi R^2}{4}V = N\frac{\pi r^2}{4}v \qquad \therefore R^2V = Nr^2v \tag{9}$$

Then, there is obtained a condition for the flow channel 10 and the nozzle hole 13 for stably generating the droplets 7 which are high in rectilinearity and small in variation in grain size from the liquid jet flow. By modifying Formula (1), Formula (10) described below is obtained.

$$rv^2 = Je\cdot\frac{\sigma}{\rho_a^{0.55}\cdot\rho^{0.45}} \tag{10}$$

Here, as Formula (11) described below, k is substituted for the right-hand side of Formula (10).

$$k = Je\cdot\frac{\sigma}{\rho_a^{0.55}\cdot\rho^{0.45}} \tag{11}$$

As described above, since it is necessary to fulfill Je≤400 for stably forming the droplet flow which is high in rectilinearity and small in variation in grain size from the liquid jet flow jetted, by substituting this condition in Formula (10), Formula (12) described below is obtained.

$$rv^2 = k \le \frac{400\sigma}{\rho_a^{0.55}\cdot\rho^{0.45}} \tag{12}$$

Further, by squaring the both sides of Formula (9), and then modifying the result, Formula (13) described below is obtained.

$$R^4V^2 = N^2r^4v^2 \qquad \therefore r^4v^2 = \frac{R^4V^2}{N^2} \tag{13}$$

Here, by dividing the both sides of Formula (10) by Formula (13), Formula (14) described below is obtained.

$$\frac{rv^2}{r^4v^2} = Je\cdot\frac{\sigma}{\rho_a^{0.55}\cdot\rho^{0.45}}\Big/\frac{R^4V^2}{N^2} = k\Big/\frac{R^4V^2}{N^2} \qquad \therefore \frac{1}{r^3} = \frac{kN^2}{R^4V^2} \tag{14}$$

Meanwhile, by substituting Formula (4) in Formula (5), and then coordinating the result, Formula (15) described below is obtained.

$$\mathrm{Re} = \frac{\rho QR}{\mu A_c} = \frac{\rho\cdot A_cV\cdot R}{\mu A_c} = \frac{\rho\cdot V\cdot R}{\mu} \qquad \therefore RV = \mathrm{Re}\cdot\frac{\mu}{\rho} = \mathrm{Re}\cdot v \tag{15}$$

Here, as Formula (16) described below, l is substituted for the right-hand side of Formula (15).

$$l = \mathrm{Re}\cdot v = \mathrm{Re}\cdot\frac{\mu}{\rho} \tag{16}$$

By squaring the both sides of Formula (15), then substituting the result in Formula (14), and then defining m to coordinate the result as in Formula (18), Formula (17) described below is obtained assuming R>0. Formula (17) represents the fact that the flow channel diameter R is proportional to a 3/2-th power of the diameter r of the nozzle hole taking m as a proportional constant.

$$R = mr^{\frac{3}{2}} \tag{17}$$

$$m = N\frac{\sqrt{k}}{l} \tag{18}$$

Here, by substituting Formula (11) and Formula (16) in Formula (18), and then defining s to coordinate the result as in Formula (20) described below, the result is expressed as Formula (19) described below.

$$m = N\cdot\sqrt{Je\cdot\frac{\sigma}{\rho_a^{0.55}\cdot\rho^{0.45}}}\Big/\mathrm{Re}\cdot\frac{\mu}{\rho} = N\cdot\frac{\rho\sqrt{Je\cdot\sigma}}{\mathrm{Re}\cdot\mu\sqrt{\rho_a^{0.55}\cdot\rho^{0.45}}} = N\cdot\frac{\rho\cdot\sigma^{\frac{1}{2}}}{\mu\cdot\rho_a^{0.275}\cdot\rho^{0.225}}\cdot\frac{\sqrt{Je}}{\mathrm{Re}} = N\cdot\frac{\rho^{0.775}\cdot\sigma^{\frac{1}{2}}}{\mu\cdot\rho_a^{0.275}}\cdot\frac{\sqrt{Je}}{\mathrm{Re}} \tag{19}$$

-continued $$S = \frac{\rho^{0.775} \cdot \sigma^{\frac{1}{2}}}{\mu \cdot \rho_a^{0.275}} \tag{20}$$

Formula (20) shows the fact that s is decided by physical property values of the liquid 3 and the air density ρa. Here, the air density ρa is about 1.293 [kg/m$^3$] at a temperature 0 °C, and hardly changes even when the temperature changes. Therefore, ρa can be assumed as a constant. Therefore, s is a constant decided by the physical properties of the liquid 3.

It should be noted that the following can be said from Formula (19).

$$m \propto \frac{\sqrt{Je}}{\mathrm{Re}}$$

Specifically, it is understood that m is proportional to $Je^{1/2}$, and is inversely proportional to Re. Therefore, it is understood that $Je^{1/2}$/Re takes a minimum value in a condition in which the jet number Je takes a minimum value, and at the same time, the Reynolds number Re takes a maximum value.

As described above, since it is necessary to fulfill $0<\mathrm{Re}\leq2300$ and $0.1<Je\leq400$ for stably forming the droplet flow which is high in rectilinearity and small in variation in grain size from the liquid jet flow jetted, Formula (21) described below is obtained.

$$\frac{\sqrt{Je}}{\mathrm{Re}} > \frac{\sqrt{0.1}}{2300} \approx 1.375 \times 10^{-4} \tag{21}$$

Further, a value of $Je^{1/2}$/Re becomes infinitely large as Re decreases. Here, a lower limit value of Re is considered. When considering a flow of air, a condition for the flow of air to be the laminar flow is generally said to be Re<0.1. Since the Reynolds number of the liquid 3 tends to be higher than the Reynolds number of a gas, it is conceivable that there is no need to substantially consider the range of Re<0.1 in the flow of the liquid 3. Therefore, when setting the substantial minimum value of the Reynolds number as Re=0.1, it is conceivable that the substantial maximum values of Je and Re are Je=400 and Re=0.1, which can be expressed as Formula (22) described below.

$$\frac{\sqrt{Je}}{\mathrm{Re}} < \frac{\sqrt{400}}{0.1} = 200 \tag{22}$$

Here, by applying a magnitude relationship of Formula (21) and Formula (22) to Formula (19), Formula (23) described below is obtained.

$$1.375\times10^{-4} s\cdot N < m < 200 s\cdot N \tag{23}$$

Further, by applying Formula (23) to Formula (17), Formula (24) described below is obtained. Formula (24) shows the fact that the flow channel diameter R can be decided by the nozzle hole diameter r and the physical properties of the liquid 3 flowing through the flow channel 10.

$$1.375 \times 10^{-4} s \cdot N \cdot r^{\frac{3}{2}} < R < 200 s \cdot N \cdot r^{\frac{3}{2}} \tag{24}$$

Figure 3:
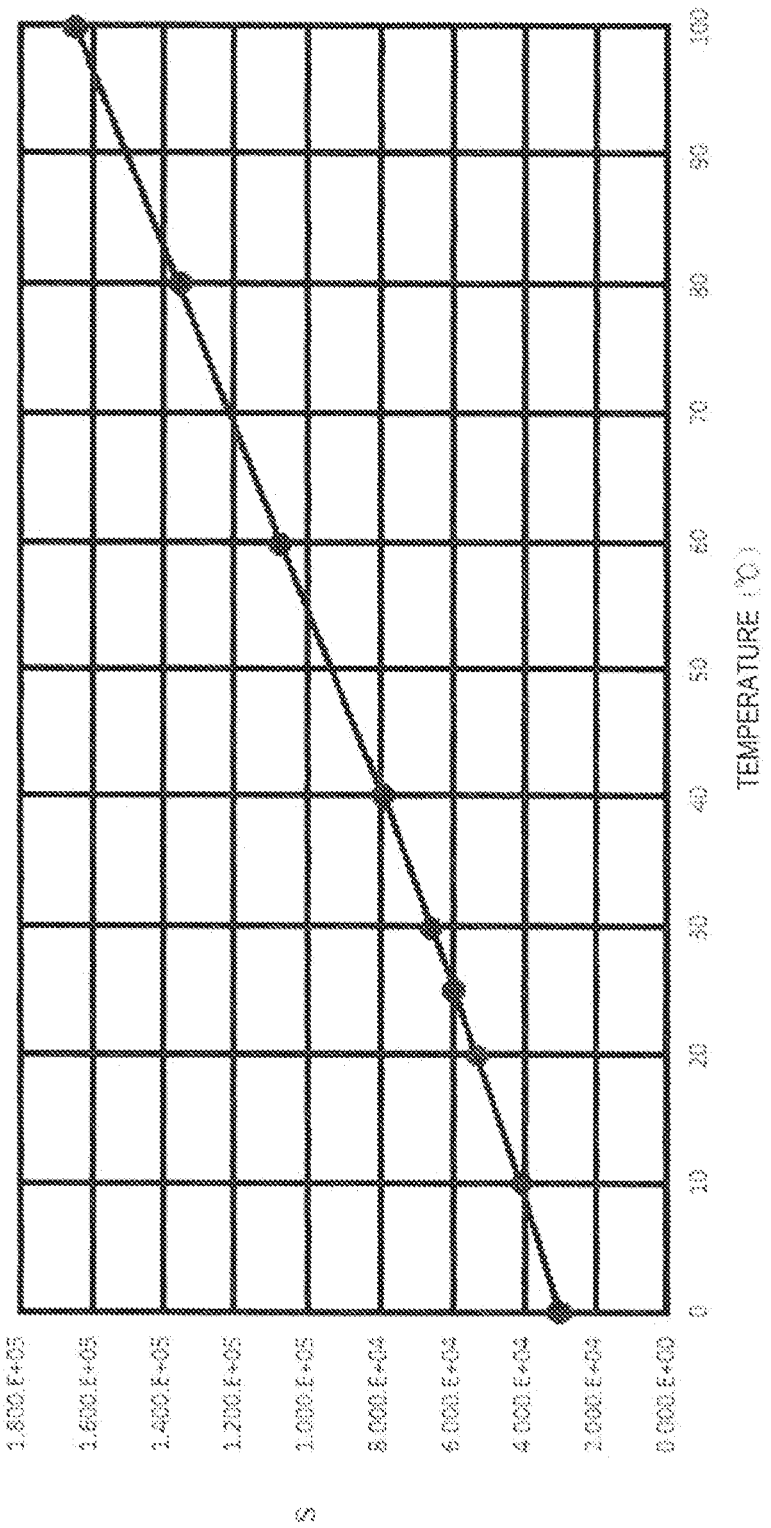
FIG. 3 is a graph with a vertical axis representing a value of s, and a horizontal axis representing temperature.

Then, a range of a numerical value which s can take will be considered. Table 1 described below shows the physical property values of water and the values of s obtained by calculation at every temperature, and FIG. 3 is a graph in which the vertical axis represents s value of water at every temperature, and the horizontal axis represents the temperature.

TABLE 1

| T(°C) | σ (N/m) | μ(Pa · s) | ρ (kg/m$^3$) | ν (m$^2$/s) | s |
|---|---|---|---|---|---|
| 0 | 0.07564 | 0.001792 | 999.84 | 1.792E−06 | 3.022.E+04 |
| 10 | 0.07422 | 0.001307 | 999.7 | 1.307E−06 | 4.104.E+04 |
| 20 | 0.07275 | 0.001002 | 998.2 | 1.004E−06 | 5.294.E+04 |
| 25 | 0.07197 | 0.000890 | 997.05 | 8.926E−07 | 5.922.E+04 |
| 30 | 0.07118 | 0.000797 | 995.65 | 8.005E−07 | 6.570.E+04 |
| 40 | 0.06959 | 0.000653 | 992.21 | 6.581E−07 | 7.907.E+04 |
| 60 | 0.06618 | 0.000467 | 983.21 | 4.750E−07 | 1.071.E+05 |
| 80 | 0.06261 | 0.000355 | 971.8 | 3.653E−07 | 1.358.E+05 |
| 100 | 0.05885 | 0.000282 | 958.35 | 2.943E−07 | 1.639.E+05 |

It can be translated from Table 1 that the s value in liquid water (0 °C through 100 °C) under ordinary pressure monotonically increases as the temperature rises. Therefore, the s value of the liquid water substantially falls within a range represented by Formula (25) described below.

$$3.02\times10^{4} < s < 16.4\times10^{4} \tag{25}$$

Figure 4:
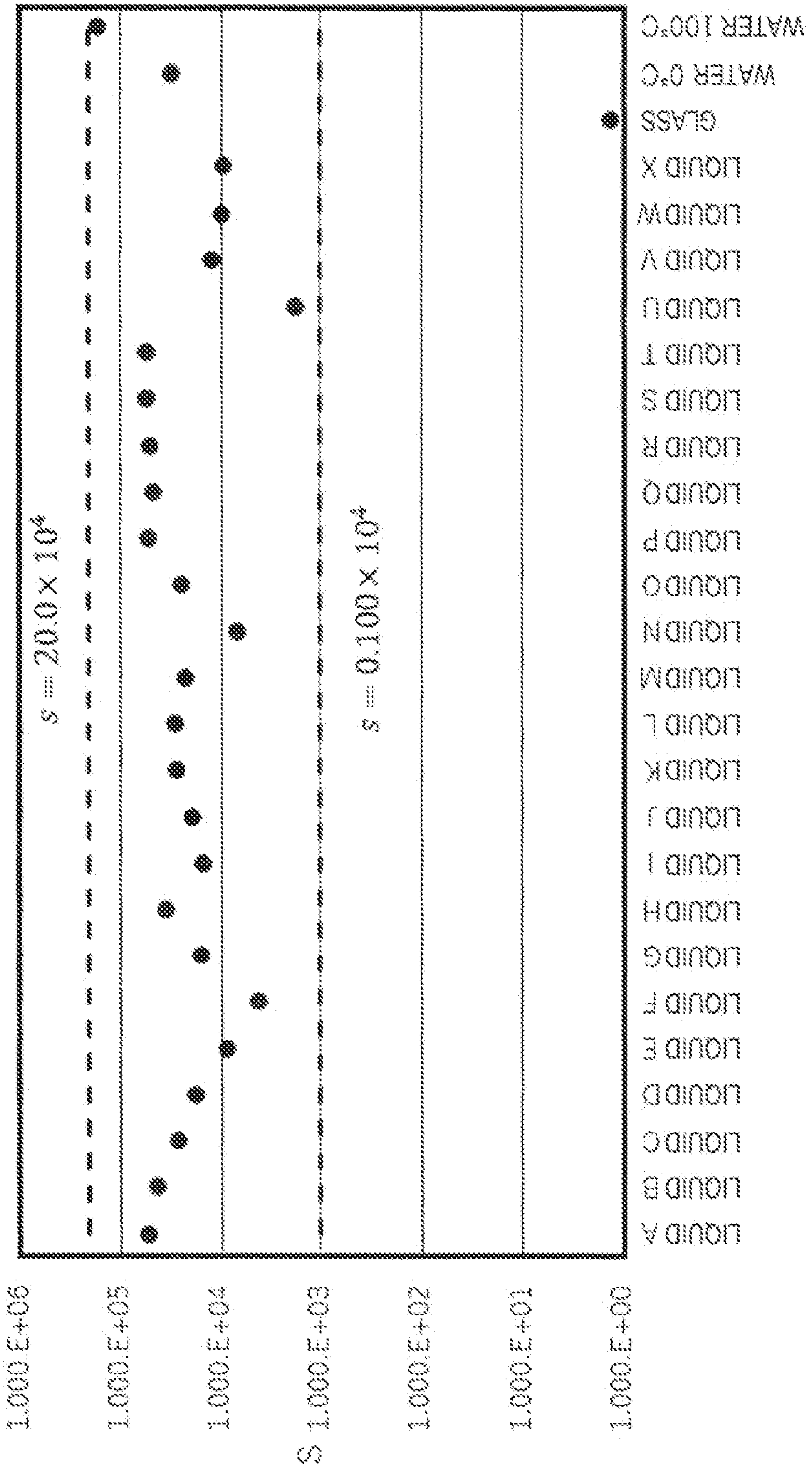
FIG. 4 is a graph with a vertical axis representing the value of s, and a horizontal axis representing a medium.

Further, Table 2 described below is a table in which physical property values of a variety of types of liquids 3 such as a commercially available lotion or hair growth tonic and glass which is heated to be liquefied, and the s values obtained using those physical property values are compiled, and FIG. 4 is a graph in which the vertical axis represents the s values in the media described in Table 2, water at 0 °C and water at 100 °C, and the horizontal axis represents the media.

TABLE 2

| MEDIUM | σ (N/m) | μ(Pa · s) | ρ (kg/m$^3$) | ν (m$^2$/s) | s |
|---|---|---|---|---|---|
| LIQUID A | 0.07062 | 0.001 | 994.5 | 1.006E−06 | 5.211.E+04 |
| LIQUID B | 0.04755 | 0.001 | 981 | 1.019E−06 | 4.231.E+04 |
| LIQUID C | 0.03985 | 0.001465 | 993 | 1.475E−06 | 2.669.E+04 |
| LIQUID D | 0.04899 | 0.002502 | 1019.5 | 2.454E−06 | 1.768.E+04 |
| LIQUID E | 0.05184 | 0.005307 | 999.5 | 5.310E−06 | 8.446.E−03 |
| LIQUID F | 0.05700 | 0.01157 | 1035 | 1.118E−05 | 4.173.E+03 |
| LIQUID G | 0.06182 | 0.003137 | 1006.5 | 3.117E−06 | 1.569.E+04 |
| LIQUID H | 0.05877 | 0.001403 | 1009 | 1.390E−06 | 3.426.E+04 |
| LIQUID I | 0.05654 | 0.00316 | 1021 | 3.095E−06 | 1.506.E+04 |
| LIQUID J | 0.05167 | 0.0024 | 1009 | 2.379E−06 | 1.878.E+04 |

TABLE 2-continued

| MEDIUM | σ (N/m) | μ(Pa · s) | ρ (kg/m³) | ν (m²/s) | s |
|---|---|---|---|---|---|
| LIQUID K | 0.04603 | 0.001552 | 988 | 1.571E–06 | 2.697.E+04 |
| LIQUID L | 0.05162 | 0.001615 | 1019 | 1.585E–06 | 2.811.E+04 |
| LIQUID M | 0.04741 | 0.001914 | 1005.5 | 1.904E–06 | 2.250.E+04 |
| LIQUID N | 0.05166 | 0.006761 | 1021.5 | 6.619E–06 | 6.731.E+03 |
| LIQUID O | 0.07175 | 0.002161 | 1013.5 | 2.132E–06 | 2.467.E+04 |
| LIQUID P | 0.07177 | 0.00101 | 1001 | 1.009E–06 | 5.227.E+04 |
| LIQUID Q | 0.07181 | 0.001138 | 999 | 1.139E–06 | 4.634.E+04 |
| LIQUID R | 0.06256 | 0.000978 | 993 | 9.846E–07 | 5.010.E+04 |
| LIQUID S | 0.07164 | 0.000971 | 991 | 9.802E–07 | 5.388.E+04 |
| LIQUID T | 0.07072 | 0.000968 | 989.5 | 9.783E–07 | 5.366.E+04 |
| LIQUID U | 0.03681 | 0.01964 | 899 | 2.185E–05 | 1.771.E+03 |
| LIQUID V | 0.03045 | 0.002668 | 924.5 | 2.886E–06 | 1.212.E+04 |
| LIQUID W | 0.02850 | 0.003176 | 883 | 3.597E–06 | 9.505.E+03 |
| LIQUID X | 0.02842 | 0.003274 | 884 | 3.704E–06 | 9.215.E+03 |
| GLASS | 1200 | 1.00E+04 | 2400 | 4.167 | 1.345.E+00 |

Table 1 and Table 2 show the fact that the s values of the variety of types of liquids except the glass substantially fall within the range of Formula (26) described below.

$$0.177\times10^4<s<5.37\times10^4 \quad (26)$$

In other words, when assuming that the liquid 3 easily available for an ordinary person is used in the droplet jet device 25, it is inferred that the s value of the liquid 3 to be made to flow through the flow channel 10 of the droplet jet device 25 substantially falls within a range represented by Formula (27) obtained by combining the ranges of Formula (25) and Formula (26).

$$0.177\times10^4<s<16.4\times10^4 \quad (27)$$

Therefore, when setting the s value to $s=0.100\times10^4$ as a value slightly smaller than the minimum value of Formula (27), an m value minimum required in the droplet jet device 25 which is generally used becomes as in Formula (28) described below. Further, by designing the flow channel diameter R and the nozzle hole diameter r of the droplet jet device 25 after setting the m value which fulfills Formula (28), it becomes possible to form a variety of types of solution into droplets to jet the droplets toward the object 9.

$$m>1.375\times10^{-4}\times0.100\times10^4\cdot N$$

$$\therefore m>0.138N \quad (28)$$

Here, since the purposes such as cleaning or crushing of the object 9 are assumed, a certain level of portability is required for the droplet jet device 25. However, as is understood from Formula (17), when increasing the m value, the flow channel diameter R also increases in proportion to the m value. Although any large amounts can be adopted as the m value within a numerical range in which Formula (28) is fulfilled, the larger the m value is made, the more the flow channel 10 grows in size unlimitedly. Since the growth in size of the droplet jet device 25 conflicts with a design concept of portability, it is preferable to decrease the upper limit value of m so that the flow channel diameter R does not become unnecessarily large. The liquid 3 which is the most difficult to spray out of the liquids 3 in Table 1 and Table 2 is water at 100 °C which has the largest s value of about $16.4\times10^4$. Table 2 shows the fact that the s values of the variety of lotions and hair growth tonics other than water are values smaller than this value. Therefore, it is inferred that by setting the s value to $s=20.0\times10^4$ as a value slightly larger than the maximum value of Formula (27), it is possible to form almost all liquids 3 which is expected to be used in general purposes into droplets to jet the droplets. Specifically, a substantial upper limit value of m when limiting the purpose of the droplet jet device 25 to general purposes is expressed as Formula (29) described below.

$$m<200\times20.0\times10^4\cdot N$$

$$\therefore m<4.00\times10^7 N \quad (29)$$

Therefore, the range of the m value which is assumed to be necessary in the droplet jet device 25 when assuming general purposes becomes as in Formula (30) described below.

$$0.138N<m<4.00\times10^7 N \quad (30)$$

Further, when applying Formula (30) to formula (17), the range of the flow channel diameter R is limited as in Formula (31).

$$0.138N < \frac{R}{r^{\frac{3}{2}}} < 4.00\times10^7 N \quad (31)$$

Here, by squaring the each side of Formula (31), and then coordinating the result, Formula (32) described below is obtained. By setting the number of the nozzle holes N, the flow channel diameter R, and the nozzle hole diameter r so as to fulfill Formula (32) described below, it is possible to form almost all liquids 3 assumed to be used for general purposes into droplets to jet the droplets, and therefore, it is possible to use the droplet jet device 25 having the flow channel 10 and the nozzle hole 13 as the cleaning equipment using the impact power caused by the liquid 3 formed into the droplets. In other words, by adopting the configuration which fulfills Formula (32), when the cross-sectional shape of the flow channel 10 is a circular shape, it is possible to spray the liquid 3 in the state of the preferable droplets 7.

$$1.90\times10^{-2} < \frac{1}{N^2}\cdot\frac{R^2}{r^3} < 1.60\times10^{15} \quad (32)$$

Here, in Table 3, there are shown measured values of a variety of parameters in the condition in which the water at each of the temperatures of 20 °C, 30 °C, and 40 °C, the liquid T, and the liquid U shown in Table 2 are actually sprayed, and can stably be formed into droplets.

TABLE 3

| LIQUID | VOLUME FLOW RATE Q ($m^3$/s) | FLOW CHANNEL CROSS-SECTIONAL AREA A ($m^2$) | KINEMATIC VISCOSITY COEFFICIENT ν ($m^2$/s) | JET VELOCITY v (m/s) | NUMBER OF NOZZLE JOLES N | Je | Re | FLOW CHANNEL DIAMETER R (m) | NOZZLE HOLE DIAMETER r (m) | $R^2/(N^2 \cdot r3)$ |
|---|---|---|---|---|---|---|---|---|---|---|
| U | 3.33·E−08 | 7.85E−07 | 2.18·E−05 | 47.0 | 1 | 73.76 | 4.86 | 1.00·E−03 | 5.00·E−05 | 8.00·E+06 |
| T | 8.33·E−08 | 3.32E−05 | 9.78·E−07 | 24.0 | 7 | 5.02 | 2.57 | 6.50·E−03 | 2.40·E−05 | 6.24·E+07 |
| WATER | 3.50·E−08 | 3.32E−05 | 1.00·E−06 | 22.7 | 7 | 2.80 | 1.05 | 6.50·E−03 | 1.50·E−05 | 2.55·E+08 |
| (20 °C) | 4.50·E−08 | 3.32E−05 | 1.00·E−06 | 27.2 | 7 | 4.03 | 1.35 | 6.50·E−03 | 1.50·E−05 | 2.55·E+08 |
| | 5.33·E−08 | 3.32E−05 | 1.00·E−06 | 34.0 | 7 | 6.29 | 1.60 | 6.50·E−03 | 1.50·E−05 | 2.55·E+08 |
| | 6.00·E−08 | 3.32E−05 | 1.00·E−06 | 35.1 | 7 | 6.72 | 1.80 | 6.50·E−03 | 1.50·E−05 | 2.55·E+08 |
| | 6.67·E−08 | 3.32E−05 | 1.00·E−06 | 41.9 | 7 | 9.57 | 2.00 | 6.50·E−03 | 1.50·E−05 | 2.55·E+08 |
| | 7.33·E−08 | 3.32E−05 | 1.00·E−06 | 43.1 | 7 | 10.10 | 2.20 | 6.50·E−03 | 1.50·E−05 | 2.55·E+08 |
| | 8.00·E−08 | 3.32E−05 | 1.00·E−06 | 49.9 | 7 | 13.54 | 2.40 | 6.50·E−03 | 1.50·E−05 | 2.55·E+08 |
| WATER | 3.50·E−08 | 3.32E−05 | 8.00·E−07 | 21.5 | 7 | 2.52 | 1.32 | 6.50·E−03 | 1.50·E−05 | 2.55·E+08 |
| (30 °C) | 4.50·E−08 | 3.32E−05 | 8.00·E−07 | 26.1 | 7 | 3.70 | 1.69 | 6.50·E−03 | 1.50·E−05 | 2.55·E+08 |
| | 5.33·E−08 | 3.32E−05 | 8.00·E−07 | 31.7 | 7 | 5.48 | 2.01 | 6.50·E−03 | 1.50·E−05 | 2.55·E+08 |
| | 6.00·E−08 | 3.32E−05 | 3.00·E−07 | 35.1 | 7 | 6.72 | 2.26 | 6.50·E−03 | 1.50·E−05 | 2.55·E+08 |
| | 6.67·E−08 | 3.32E−05 | 8.00·E−07 | 41.9 | 7 | 9.57 | 2.51 | 6.50·E−03 | 1.50·E−05 | 2.55·E+08 |
| | 7.33·E−08 | 3.32E−05 | 8.00·E−07 | 46.5 | 7 | 11.75 | 2.76 | 6.50·E−03 | 1.50·E−05 | 2.55·E+08 |
| | 3.00·E−08 | 3.32E−05 | 8.00·E−07 | 49.9 | 7 | 13.54 | 3.01 | 6.50·E−03 | 1.50·E−05 | 2.55·E+08 |
| WATER | 3.50·E−08 | 3.32E−05 | 6.58·E−07 | 21.5 | 7 | 2.52 | 1.60 | 6.50·E−03 | 1.50·E−05 | 2.55·E+08 |
| (40 °C) | 4.50·E−08 | 3.32E−05 | 6.58·E−07 | 26.1 | 7 | 3.70 | 2.06 | 6.50·E−03 | 1.50·E−05 | 2.55·E+08 |
| | 5.33·E−08 | 3.32E−05 | 6.58·E−07 | 35.1 | 7 | 6.72 | 2.44 | 6.50·E−03 | 1.50·E−05 | 2.55·E+08 |
| | 6.00·E−08 | 3.32E−05 | 6.58·E−07 | 36.3 | 7 | 7.16 | 2.75 | 6.50·E−03 | 1.50·E−05 | 2.55·E+08 |
| | 6.67·E−08 | 3.32E−05 | 6.58·E−07 | 43.1 | 7 | 10.10 | 3.05 | 6.50·E−03 | 1.50·E−05 | 2.55·E+08 |
| | 7.33·E−08 | 3.32E−05 | 6.58·E−07 | 47.6 | 7 | 12.33 | 3.36 | 6.50·E−03 | 1.50·E−05 | 2.55·E+08 |
| | 8.00·E−08 | 3.32E−05 | 6.58·E−07 | 51.0 | 7 | 14.16 | 3.66 | 6.50·E−03 | 1.50·E−05 | 2.55·E+08 |

As is understood when referring to Table 3, from the parameters obtained by an experiment, the values of Je and Re fall within ranges of the values taken as the data of the calculation in the present disclosure. Further, it is understood that the value of $R^2/(N^2 \cdot r^3)$ obtained from the design values of the flow channel and the nozzle hole 13 with which these liquids can stably be formed into droplets and then jetted fulfills Formula (32). Therefore, it is understood that Formula (32) appropriately represents the condition necessary for the actual droplet jet.

Here, Table 4 shows a minimum value and a maximum value of the flow channel diameter R allowed in Formula (32) when specifically setting the nozzle hole diameter r in the droplet jet device 25 using a single nozzle hole 13 (N=1).

TABLE 4

| NOZZLE HOLE DIAMETER (μm) | MINIMUM FLOW CHANNEL DIAMETER (mm) | MAXIMUM FLOW CHANNEL DIAMETER (mm) |
|---|---|---|
| 1 | 1.38E−07 | 4.00E+01 |
| 5 | 5.45E−07 | 1.58E+02 |
| 10 | 1.54E−06 | 4.47E+02 |
| 20 | 4.36E−06 | 1.26E+03 |
| 30 | 8.01E−06 | 2.32E+03 |
| 40 | 1.23E−05 | 3.58E+03 |
| 50 | 1.72E−05 | 5.00E+03 |
| 60 | 2.26E−05 | 6.57E+03 |
| 70 | 2.85E−05 | 8.28E+03 |
| 80 | 3.49E−05 | 1.01E+04 |
| 90 | 4.16E−05 | 1.21E+04 |
| 100 | 4.87E−05 | 1.41E+04 |
| 110 | 5.62E−05 | 1.63E+04 |
| 120 | 6.41E−05 | 1.86E+04 |
| 130 | 7.22E−05 | 2.10E+04 |
| 140 | 8.07E−05 | 2.34E+04 |
| 150 | 8.95E−05 | 2.60E+04 |
| 160 | 9.86E−05 | 2.86E+04 |
| 170 | 1.08E−04 | 3.13E+04 |
| 180 | 1.18E−04 | 3.42E+04 |
| 190 | 1.28E−04 | 3.70E+04 |
| 200 | 1.38E−04 | 4.00E+04 |
| 300 | 2.53E−04 | 7.35E+04 |
| 400 | 3.90E−04 | 1.13E+05 |
| 500 | 5.45E−04 | 1.58E+05 |
| 600 | 7.16E−04 | 2.08E+05 |
| 700 | 9.03E−04 | 2.62E+05 |
| 800 | 1.10E−03 | 3.20E+05 |
| 900 | 1.32E−03 | 3.82E+05 |
| 1000 | 1.54E−03 | 4.47E+05 |

Incidentally, the liquid U in Table 2 and Table 3 is a liquid the largest in value of the kinematic viscosity coefficient ν of the liquids 3 the physical property values of which are shown in the present specification. The liquid U shows the largest value in Je and Re out of the liquids 3 a variety of parameters of which are actually measured, but the values are Je=73.76 and Re=4.86 at largest, which are significantly smaller compared to Je=400 as the upper limit value of Je and Re=2300 as the upper limit value of Re. Further, the liquid T in Table 2 and Table 3 is a liquid the smallest in value of the kinematic viscosity coefficient ν of the liquids 3 the physical property values of which are shown in the present specification. The values of Je and Re of the liquid T are Je=5.02 and Re=2.57, respectively.

Therefore, the numerical ranges of $0.1<Je\leq400$ and $0.1<Re\leq2300$ used for derivation of Formula (32) are too broad in some cases. Therefore, by narrowing the ranges of Je and Re, there is obtained a range of the flow channel diameter R which is realistic and is suitable for the actual droplet jet device 25. Here, based on the values of Je and Re which are obtained by the experiment shown in Table 3, the ranges of Je and Re are set as $1\leq Je\leq100$, $1\leq Re\leq100$. Then, Formula (21) and Formula (22) are rewritten as Formula (33) described below and Formula (34) described below, and as a result, Formula (35) described below corresponding to Formula (23) is obtained.

$$\frac{\sqrt{Je}}{\mathrm{Re}} > \frac{\sqrt{1}}{100} = 0.01 \tag{33}$$

$$\frac{\sqrt{Je}}{\mathrm{Re}} < \frac{\sqrt{100}}{1} = 10 \tag{34}$$

$$0.01s \cdot N < m < 10s \cdot N \tag{35}$$

Here, when applying the range of s of Formula (27) to formula (35), it is possible to narrow down the range of m as Formula (36) described below.

$$0.01 \times 0.177 \times 10^4 N < m < 10 \times 16.4 \times 10^4 N$$

$$\therefore 17.7N < m < 1.64 \times 10^6 N \tag{36}$$

Here, by rewriting Formula (36) into a shape similar to Formula (32), Formula (37) described below is obtained.

$$17.7N < \frac{R}{r^{\frac{3}{2}}} < 1.64 \times 10^6 N \tag{37}$$

$$\therefore 3.13 \times 10^2 < \frac{1}{N^2} \cdot \frac{R^2}{r^3} < 2.69 \times 10^{12}$$

Formula (37) also represents the numerical range including all of the values of $R^2/(N^2 \cdot r^3)$ obtained based on the experimental values shown in Table 3. In other words, by adopting the configuration which fulfills Formula (37), when the cross-sectional shape of the flow channel 10 is a circular shape, it is possible to spray the liquid 3 in the state of the preferable droplets 7 using almost all liquids 3 to be used generally. Table 5 shows the minimum value and the maximum value of the flow channel diameter R allowed in Formula (37) when specifically setting the nozzle hole diameter r in the droplet jet device 25 using the single nozzle hole 13 (N=1).

TABLE 5

| NOZZLE HOLE DIAMETER (μm) | MINIMUM FLOW CHANNEL DIAMETER (mm) | MAXIMUM FLOW CHANNEL DIAMETER (mm) |
|---|---|---|
| 1 | 1.77.E−05 | 1.64.E+00 |
| 5 | 1.98.E−04 | 1.83.E+01 |
| 10 | 5.59.E−04 | 5.19.E+01 |
| 20 | 1.58.E−03 | 1.47.E−02 |
| 30 | 2.91.E−03 | 2.69.E−02 |
| 40 | 4.48.E−03 | 4.15.E+02 |
| 50 | 6.25.E−03 | 5.80.E+02 |
| 60 | 8.22.E−03 | 7.62.E+02 |
| 70 | 1.04.E−02 | 9.61.E+02 |
| 80 | 1.27.E−02 | 1.17.E+03 |
| 90 | 1.51.E−02 | 1.40.E+03 |
| 100 | 1.77.E−02 | 1.64.E+03 |
| 110 | 2.04.E−02 | 1.89.E+03 |
| 120 | 2.33.E−02 | 2.16.E+03 |
| 130 | 2.62.E−02 | 2.43.E+03 |
| 140 | 2.93.E−02 | 2.72.E−03 |
| 150 | 3.25.E−02 | 3.01.E+03 |
| 160 | 3.58.E−02 | 3.32.E+03 |
| 170 | 3.92.E−02 | 3.64.E−03 |
| 180 | 4.27.E−02 | 3.96.E+03 |
| 190 | 4.63.E−02 | 4.30.E+03 |
| 200 | 5.00.E−02 | 4.64.E+03 |
| 300 | 9.19.E−02 | 8.52.E+03 |
| 400 | 1.42.E−01 | 1.31.E+04 |
| 500 | 1.98.E−01 | 1.83.E+04 |
| 600 | 2.60.E−01 | 2.41.E+04 |
| 700 | 3.28.E−01 | 3.04.E+04 |

TABLE 5-continued

| NOZZLE HOLE DIAMETER (μm) | MINIMUM FLOW CHANNEL DIAMETER (mm) | MAXIMUM FLOW CHANNEL DIAMETER (mm) |
|---|---|---|
| 800 | 4.00.E−01 | 3.71.E+04 |
| 900 | 4.78.E−01 | 4.43.E+04 |
| 1000 | 5.59.E−01 | 5.19.E+04 |

Further, it is understood from the result in Table 3 that when specializing the droplet jet device 25 in performing cleaning of a skin using, for example, water alone, the range of Formula (37) is too much. This is caused by the fact that the range of the s value of water is narrower than the range of the s value shown in Formula (23). Further, when the droplet jet device 25 is used for the purpose of skin cleaning, since the object which the droplets collide with is a human skin, there is no chance that the water at such a high temperature as 60 °C through 100 °C is used. Therefore, in the case of the droplet jet device 25 intended to perform the skin cleaning with water, what is sprayed is limited to the water at the temperature in a range of about 20 °C through 40 °C. In this condition, according to Table 1, the s value is narrowed down to the range of Formula (38).

$$5.3 \times 10^4 < s < 7.9 \times 10^4 \tag{38}$$

Further, since the ranges of Je and Re of water in the temperature range described above can be set as $1 \le Je \le 15$, $1 \le Re \le 10$ according to Table 3, the expression of Formula (39) described below and Formula (40) described below is possible, and the range of m under this condition becomes to be expressed as Formula (41).

$$\frac{\sqrt{Je}}{\mathrm{Re}} > \frac{\sqrt{1}}{10} = 0.100 \tag{39}$$

$$\frac{\sqrt{Je}}{\mathrm{Re}} < \frac{\sqrt{15}}{1} \approx 3.87 \tag{40}$$

$$0.100 \times 5.3 \times 10^4 N < m < 3.87 \times 7.9 \times 10^4 N \tag{41}$$

$$\therefore 0.53 \times 10^4 N < m < 30.6 \times 10^4 N$$

Here, by rewriting Formula (41) into a shape similar to Formula (32) and Formula (37), Formula (42) described below is obtained.

$$0.53 \times 10^4 N < \frac{R}{r^{\frac{3}{2}}} < 30.6 \times 10^4 N \tag{42}$$

$$\therefore 2.81 \times 10^7 < \frac{1}{N^2} \cdot \frac{R^2}{r^3} < 9.36 \times 10^{10}$$

Formula (42) represents the numerical range including all of the values of $R^2/(N^2 \cdot r^3)$ obtained based on the experimental values of the water in a range of 20 °C through 40 °C shown in Table 3. In other words, by adopting the configuration which fulfills Formula (42), when the cross-sectional shape of the flow channel 10 is a circular shape, it is possible to spray the liquid 3 in the state of the preferable droplets 7 using the water at the temperature no lower than 20 °C and no higher than 40 °C, and the liquids 3 similar in characteristics to that water. Table 6 shows the minimum value and the maximum value of the flow channel diameter R allowed in Formula (37) when specifically setting the nozzle hole diameter r in the droplet jet device 25 using the single nozzle hole 13 (N=1).

TABLE 6

| NOZZLE HOLE DIAMETER W | MINIMUM FLOW CHANNEL DIAMETER (mm) | MAXIMUM FLOW CHANNEL DIAMETER (mm) |
|---|---|---|
| 1 | 5.30.E−03 | 3.06.E−01 |
| 5 | 5.93.E−02 | 3.42.E+00 |
| 10 | 1.68.E−01 | 9.67.E+00 |
| 20 | 4.74.E−01 | 2.74.E+01 |
| 30 | 8.71.E−01 | 5.03.E+01 |
| 40 | 1.34.E+00 | 7.74.E+01 |
| 50 | 1.87.E+00 | 1.08.E+02 |
| 60 | 2.46.E+00 | 1.42.E+02 |
| 70 | 3.10.E+00 | 1.79.E+02 |
| 80 | 3.79.E+00 | 2.19.E+02 |
| 90 | 4.53.E+00 | 2.61.E+02 |
| 100 | 5.30.E+00 | 3.06.E+02 |
| 110 | 6.12.E+00 | 3.53.E+02 |
| 120 | 6.97.E+00 | 4.02.E+02 |
| 130 | 7.86.E+00 | 4.53.E+02 |
| 140 | 8.78.E+00 | 5.07.E+02 |
| 150 | 9.74.E+00 | 5.62.E+02 |
| 160 | 1.07.E+01 | 6.19.E+02 |
| 170 | 1.17.E+01 | 6.78.E+02 |
| 180 | 1.28.E+01 | 7.39.E+02 |
| 190 | 1.39.E+01 | 8.01.E+02 |
| 200 | 1.50.E+01 | 8.65.E+02 |
| 300 | 2.75.E+01 | 1.59.E+03 |
| 400 | 4.24.E+01 | 2.45.E+03 |
| 500 | 5.93.E+01 | 3.42.E+03 |
| 600 | 7.79.E+01 | 4.50.E+03 |
| 700 | 9.82.E+01 | 5.67.E+03 |
| 800 | 1.20.E+02 | 6.92.E+03 |
| 900 | 1.43.E+02 | 8.26.E+03 |
| 1000 | 1.68.E+02 | 9.67.E+03 |

Control Example when Flow Channel has Rectangular Shape

Figure 5:
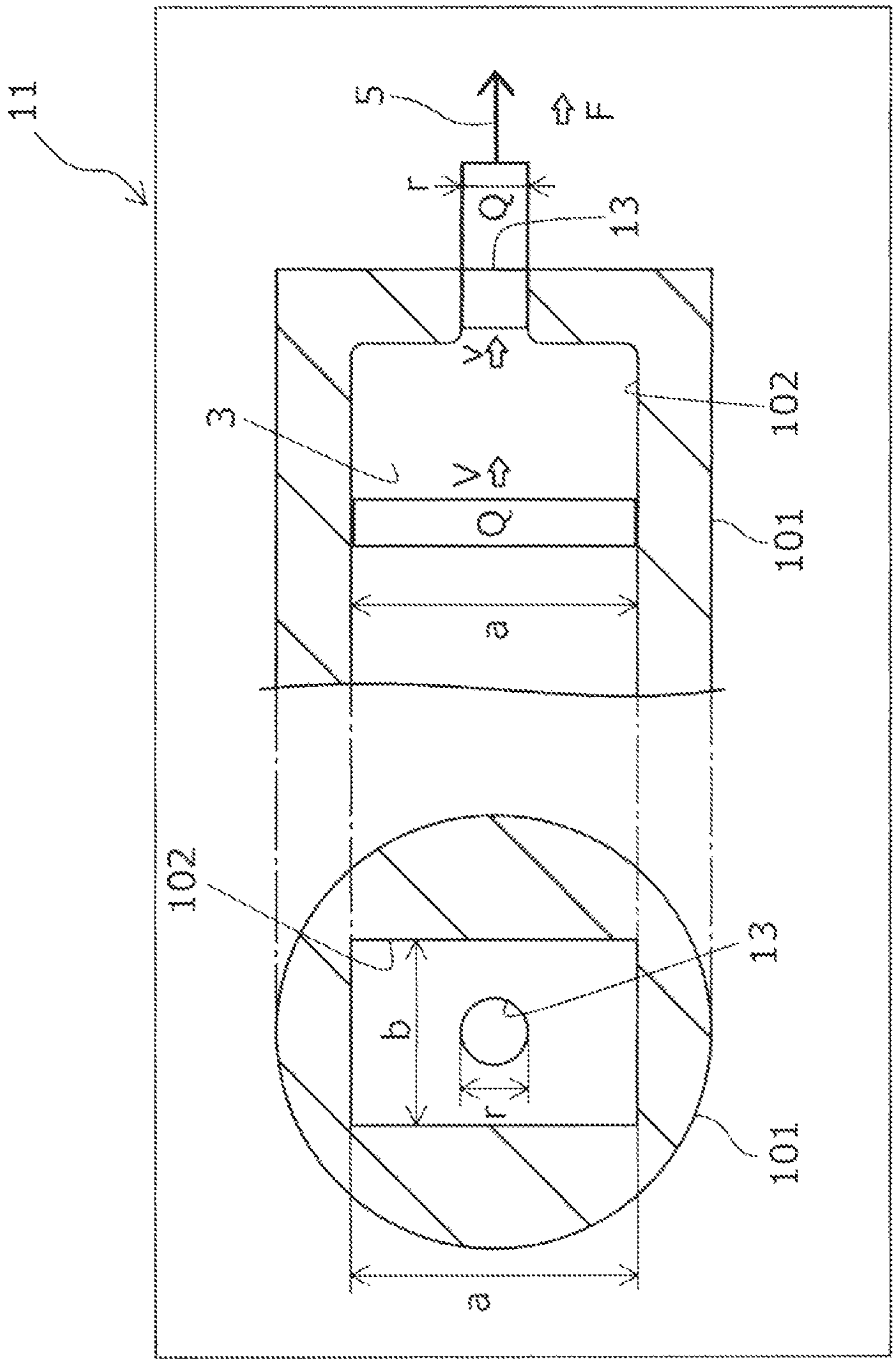
FIG. 5 is a schematic diagram of the jet nozzle when the cross-sectional shape of the flow channel is a rectangular shape.

Then, there will be described when the cross-sectional shape of the flow channel 10 is not the circular shape, but is a rectangular shape. Here, in FIG. 5, a left-hand diagram is a schematic diagram viewed from an ejection direction of the droplets 7, and a right-hand diagram is a side cross-sectional view corresponding to the left-hand diagram. In FIG. 5, the following parameters are schematically expressed so as to visually be recognized. It should be noted that the expression that the shape of the flow channel is a circular shape means that the cross-sectional shape of the flow channel 10 in a portion adjacent to the jet nozzle 11 is a rectangular shape, and means that the cross-sectional shape of the flow channel inner wall 102 is a rectangular shape as shown in the left-hand diagram in FIG. 5. It should be noted that the shape of the flow channel outer wall 101 is not particularly limited. What is affected by the cross-sectional shape of the flow channel 10 is the hydraulic diameter DH represented by Formula (3). A defining formula of the hydraulic diameter DH is expressed as Formula (43) described below. Here, L is a wet-edge length of the flow channel 10, and is a contour length of the flow channel inner wall 102 on the cross-sectional surface of the flow channel 10 in another expression.

$$D_H = \frac{4A_c}{L} \tag{43}$$

When the cross-sectional surface has a rectangular shape having long sides a [m] and short sides b [m], since Ac=ab, L=2(a+b) are true, DH is expressed as Formula (44) described below.

$$D_H = \frac{4ab}{2(a+b)} = \frac{2ab}{a+b} \tag{44}$$

By substituting Formula (44) in Formula (2), Formula (45) described below is obtained.

$$\mathrm{Re} = \frac{Q\cdot\frac{2ab}{a+b}}{vA_c} = \frac{\rho Q\cdot\frac{2ab}{a+b}}{\mu A_c} \tag{45}$$

Since an equation of continuity is true between the flow channel 10 and the nozzle hole 13 even when the cross-sectional surface of the flow channel 10 has the rectangular shape, Formula (5) is fulfilled. Further, since the condition of the nozzle hole 13 is substantially the same as when the flow channel 10 has the circular shape, the total cross-sectional area A of the nozzle holes 13 fulfills Formula (6), and the cross-sectional area An of each of the nozzle holes 13 fulfills Formula (8). Therefore, Formula (46) described below is derived.

$$Q = abV = N\frac{\pi r^2}{4}v \qquad \therefore \frac{4ab}{\pi}V = Nr^2 v \tag{46}$$

Further, by squaring the both sides of Formula (46), and then modifying the formula, Formula (47) described below is obtained.

$$\left(\frac{4ab}{\pi}\right)^2 V^2 = N^2 r^4 v^2 \qquad \therefore r^4 v^2 = \frac{\left(\frac{4ab}{\pi}\right)^2 V^2}{N^2} \tag{47}$$

Further, by dividing the both sides of Formula (10) by Formula (47), Formula (48) described below is obtained.

$$\frac{rv^2}{r^4 v^2} = Je\cdot\frac{\sigma}{\rho_a^{0.55}\cdot\rho^{0.45}} \Big/ \frac{\left(\frac{4ab}{\pi}\right)^2 V^2}{N^2} = k \Big/ \frac{\left(\frac{4ab}{\pi}\right)^2 V^2}{N^2} \qquad \therefore \frac{1}{r^3} = \frac{kN^2}{\left(\frac{4ab}{\pi}\right)^2 V^2} \tag{48}$$

Meanwhile, by further modifying Formula (45), Formula (49) described below is obtained.

$$\mathrm{Re} = \frac{\rho Q\frac{2ab}{a+b}}{\mu A_c} = \frac{\rho\cdot A_c V\cdot\frac{2ab}{a+b}}{\mu A_c} = \frac{\rho\cdot V\cdot\frac{2ab}{a+b}}{\mu} \tag{49}$$

-continued $$\frac{2ab}{a+b}V = \mathrm{Re}\cdot\frac{\mu}{\rho} = \mathrm{Re}\cdot v = l$$

$$\therefore 4abV = 2(a+b)l$$

Further, by squaring the both sides of Formula (49), then substituting the result in Formula (48), and then coordinating the result, Formula (50) described below is obtained.

$$\frac{1}{r^3} = \frac{kN^2}{\left\{\frac{2(a+b)}{\pi}\right\}^2 l^2} \Rightarrow \left\{\frac{2(a+b)}{\pi}\right\}^2 = \frac{kN^2}{l^2}r^3 \tag{50}$$

$$\therefore \frac{2(a+b)}{\pi} = mr^{\frac{3}{2}}$$

The subsequent calculation is the same as when the flow channel 10 has the circular shape. In other words, there is nothing more than the replacement of R in Formula (17) by 2(a+b)/π. This corresponds to the change from the contour length πR of the flow channel inner wall 102 when the cross-sectional surface of the flow channel 10 has the circular shape to the contour length 2(a+b) of the flow channel inner wall 102 due to the change of the cross-sectional shape of the flow channel 10 to the rectangular shape. Therefore, when the cross-sectional shape of the flow channel 10 is the rectangular shape, Formula (51) corresponding to Formula (32) becomes as follows.

$$1.90\times10^{-2} < \frac{1}{N^2}\cdot\frac{\left\{\frac{2(a+b)}{\pi}\right\}^2}{r^3} < 1.60\times10^{15} \tag{51}$$

Here, by arranging the shape of Formula (51), since $\pi^2$ is about 9.87, Formula (52) described below is obtained. As described above, by adopting the configuration which fulfills Formula (52), when the cross-sectional shape of the flow channel 10 is the rectangular shape, it is possible to spray the liquid 3 in the state of the preferable droplets 7.

$$4.75\times10^{-3}\pi^2 < \frac{1}{N^2}\cdot\frac{(a+b)^2}{r^3} < 4.00\times10^{14} \tag{52}$$

$$\therefore 4.69\times10^{-2} < \frac{1}{N^2}\cdot\frac{(a+b)^2}{r^3} < 3.95\times10^{15}$$

It should be noted that, in a similar manner, Formula (54) corresponding to Formula (37) changes to the following via Formula (53) described below. As described above, by adopting the configuration which fulfills Formula (54), it is possible to spray the liquid 3 in the state of the preferable droplets 7 using almost all liquids 3 to be used generally.

$$3.13\times10^{2} < \frac{1}{N^2}\cdot\frac{\left\{\frac{2(a+b)}{\pi}\right\}^2}{r^3} < 2.69\times10^{12} \tag{53}$$

$$78.3\pi^2 < \frac{1}{N^2}\cdot\frac{(a+b)^2}{r^3} < 6.73\times10^{11}\pi^2$$

$$\therefore 7.73\times10^{2} < \frac{1}{N^2}\cdot\frac{(a+b)^2}{r^3} < 6.64\times10^{12} \tag{54}$$

Further, in a similar manner, Formula (55) corresponding to Formula (42) changes to the following. As described above, by adopting the configuration which fulfills Formula (54), when the cross-sectional shape of the flow channel 10 is a rectangular shape, it is possible to spray the liquid 3 in the state of the preferable droplets 7 using the water at the temperature no lower than 20 °C and no higher than 40 °C, and the liquids 3 similar in characteristics to that water.

$$2.81\times10^{7} < \frac{1}{N^2}\cdot\frac{\left\{\frac{2(a+b)}{\pi}\right\}^2}{r^3} < 9.36\times10^{10} \tag{55}$$

$$7.03\times10^{6}\pi^2 < \frac{1}{N^2}\cdot\frac{R^2}{r^3} < 2.34\times10^{10}\pi^2$$

$$\therefore 2.77\times10^{7} < \frac{1}{N^2}\cdot\frac{(a+b)^2}{r^3} < 2.31\times10^{11}$$

Figure 6:
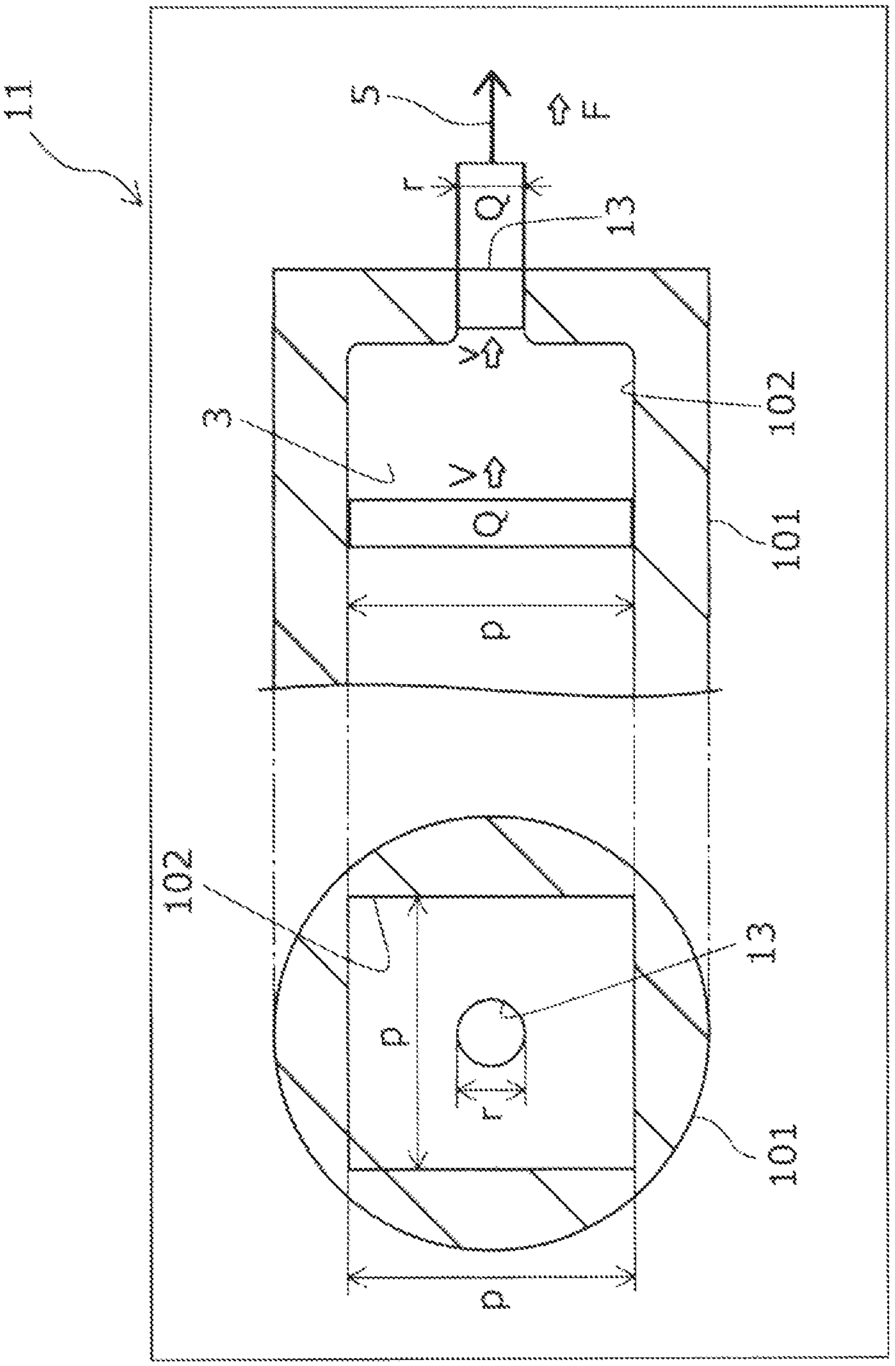
FIG. 6 is a schematic diagram of the jet nozzle when the cross-sectional shape of the flow channel is a square shape.

Here, there will be described when the cross-sectional shape of the flow channel 10 is a square shape. In FIG. 6, a left-hand diagram is a schematic diagram viewed from an ejection direction of the droplets 7, and a right-hand diagram is a side cross-sectional view corresponding to the left-hand diagram. In FIG. 6, the following parameters are schematically expressed so as to visually be recognized. It should be noted that the expression that the shape of the flow channel is a square shape means that the cross-sectional shape of the flow channel 10 in a portion adjacent to the jet nozzle 11 is a square shape, and means that the cross-sectional shape of the flow channel inner wall 102 is a square shape as shown in the left-hand diagram in FIG. 6. It should be noted that the shape of the flow channel outer wall 101 is not particularly limited. When the cross-sectional shape of the flow channel 10 is the square shape, defining the length of each side as p [m], since p=a=b is true, it is possible to replace a+b in Formula (52), Formula (54), and Formula (55) with 2p, and thus, Formula (58) described below is obtained from Formula (56) described below. As described above, by adopting the configuration which fulfills Formula (58), when the cross-sectional shape of the flow channel 10 is the square shape, it is possible to spray the liquid 3 in the state of the preferable droplets 7.

$$4.69\times10^{-2} < \frac{1}{N^2}\cdot\frac{(2p)^2}{r^3} < 3.95\times10^{15} \tag{56}$$

$$\therefore 1.17\times10^{-2} < \frac{1}{N^2}\cdot\frac{p^2}{r^3} < 9.88\times10^{14}$$

$$7.73\times10^{2} < \frac{1}{N^2}\cdot\frac{(2p)^2}{r^3} < 6.64\times10^{12} \tag{57}$$

$$\therefore 1.93\times10^{2} < \frac{1}{N^2}\cdot\frac{p^2}{r^3} < 1.66\times10^{12}$$

$$2.77\times10^{7} < \frac{1}{N^2}\cdot\frac{(2p)^2}{r^3} < 2.31\times10^{11} \tag{58}$$

$$\therefore 6.93\times10^{6} < \frac{1}{N^2}\cdot\frac{p^2}{r^3} < 5.78\times10^{10}$$

Control Example when Generalizing Cross-Sectional Shape of Flow Channel

Figure 7:
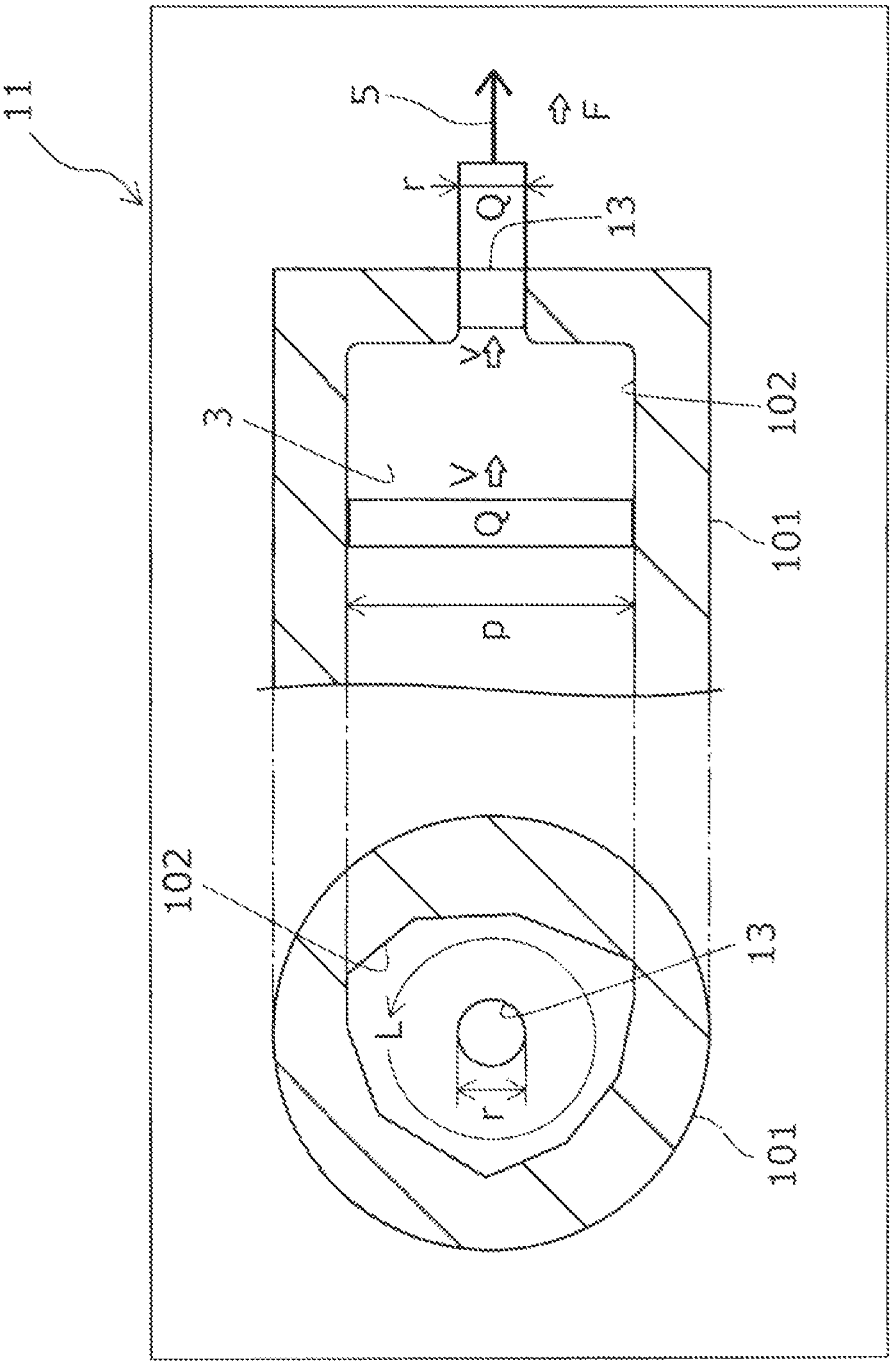
FIG. 7 is a schematic diagram of the jet nozzle when the cross-sectional shape of the flow channel is a polygonal shape.

Further, there will be made a consideration generalizing the cross-sectional shape of the flow channel 10 without specifying the cross-sectional shape of the flow channel 10. Here, in FIG. 7, a left-hand diagram is a schematic diagram viewed from an ejection direction of the droplets 7, and a right-hand diagram is a side cross-sectional view corresponding to the left-hand diagram. In FIG. 7, the following parameters are schematically expressed so as to visually be recognized. It should be noted that FIG. 7 shows an example of when the cross-sectional shape of the flow channel 10 is a polygonal shape. The cross-sectional shape of the flow channel 10 is not limited to the polygonal shape, and can include an arbitrary curved portion. By substituting Formula (43) as the defining formula of the hydraulic diameter DH directly in Formula (2), Formula (59) described below is obtained.

$$\mathrm{Re} = \frac{Q \cdot \frac{4A_c}{L}}{vA_c} = \frac{\rho Q \cdot \frac{4A_c}{L}}{\mu A_c} \tag{59}$$

Formula (5) is true between the flow channel 10 and the nozzle hole 13 irrespective of the cross-sectional shape of the flow channel 10. Further, since the condition of the nozzle hole 13 is substantially the same as when the cross-sectional shape of the flow channel is the circular shape and when the cross-sectional shape of the flow channel is the rectangular shape, the total cross-sectional area A of the nozzle holes 13 fulfills Formula (6), and the cross-sectional area An of each of the nozzle holes 13 fulfills Formula (8). Therefore, Formula (60) described below is derived.

$$Q = A_c V = N\frac{\pi r^2}{4}v \qquad \therefore \frac{4A_c}{\pi}V = Nr^2 v \tag{60}$$

Further, by squaring the both sides of Formula (60), and then modifying the result, Formula (61) described below is obtained.

$$\left(\frac{4A_c}{\pi}\right)^2 V^2 = N^2 r^4 v^2 \qquad \therefore r^4 v^2 = \frac{\left(\frac{4A_c}{\pi}\right)^2 V^2}{N^2} \tag{61}$$

Further, by dividing the both sides of Formula (10) by Formula (61), Formula (62) described below is obtained.

$$\frac{rv^2}{r^4v^2} = Je \cdot \frac{\sigma}{\rho_a^{0.55} \cdot \rho^{0.45}} \Big/ \frac{\left(\frac{4A_c}{\pi}\right)^2 V^2}{N^2} = k \Big/ \frac{\left(\frac{4A_c}{\pi}\right)^2 V^2}{N^2} \qquad \therefore \frac{1}{r^3} = \frac{kN^2}{\left(\frac{4A_c}{\pi}\right)^2 V^2} \tag{62}$$

Meanwhile, by further modifying Formula (59), Formula (63) described below is obtained.

$$\mathrm{Re} = \frac{\rho Q \cdot \frac{4A_c}{L}}{\mu A_c} = \frac{\rho \cdot A_c V \cdot \frac{4A_c}{L}}{\mu A_c} = \frac{\rho \cdot V \cdot \frac{4A_c}{L}}{\mu} \qquad \frac{4A_c}{L}V = \mathrm{Re} \cdot \frac{\mu}{\rho} = \mathrm{Re} \cdot v = l \qquad \therefore 4A_c V = L \cdot l \tag{63}$$

Here, by squaring the both sides of Formula (63), then substituting the result in Formula (62), and then coordinating the result, Formula (64) described below is obtained.

$$\frac{1}{r^3} = \frac{kN^2}{\left\{\frac{L}{\pi}\right\}^2 l^2} \Rightarrow \left(\frac{L}{\pi}\right)^2 = \frac{kN^2}{l^2}r^3 \qquad \therefore \frac{L}{\pi} = mr^{\frac{3}{2}} \tag{64}$$

The subsequent calculation is the same as when the cross-sectional shape of the flow channel 10 is the circular shape. In other words, there is nothing more than the replacement of R in Formula (17) by L/π. Actually, when the cross-sectional shape of the flow channel 10 is the circular shape, since the contour length L of the flow channel inner wall 102 is L=πR, the left-hand side of Formula (64) becomes L/π=πR/π=R, and thus, Formula (17) is obtained. Further, when the cross-sectional shape of the flow channel 10 is the rectangular shape, since the contour length L of the flow channel inner wall 102 is L=2(a+b), the left-hand side of Formula (64) becomes L/π=2(a+b)/π, and thus, Formula (50) is obtained. In essence, it is derived from the defining formulas of the jet number Je and the Reynolds number Re alone that the contour length L of the flow channel inner wall 102 is proportional to the 3/2-th power of the nozzle hole diameter r irrespective of the cross-sectional shape of the flow channel 10. Further, it is also understood at the same time that the proportional constant on this occasion is mπ. Further, it also shows that it is possible to limit a possible range of a value of a ratio between the contour length L of the flow channel inner wall 102 on the cross-sectional surface of the flow channel 10 and the 3/2-th power of the nozzle hole diameter r based on the two conditions, namely "the liquid 3 sprayed forms droplets," and "the flow in the flow channel 10 is a laminar flow." By generalizing Formula (32), Formula (37), and Formula (42) based on the fact described above, Formula (65) through Formula (67) described below are obtained. It should be noted that here the calculation is performed assuming $\pi^2$ as 9.87.

$$1.90\times10^{-2} < \frac{1}{N^2}\cdot\frac{\left(\frac{L}{\pi}\right)^2}{r^3} < 1.60\times10^{15} \qquad 1.90\times10^{-2}\pi^2 < \frac{1}{N^2}\cdot\frac{L^2}{r^3} < 1.60\times10^{15}\pi^2 \qquad \therefore 0.188 < \frac{1}{N^2}\cdot\frac{L^2}{r^3} < 1.58\times10^{16} \tag{65}$$

Figure 8:
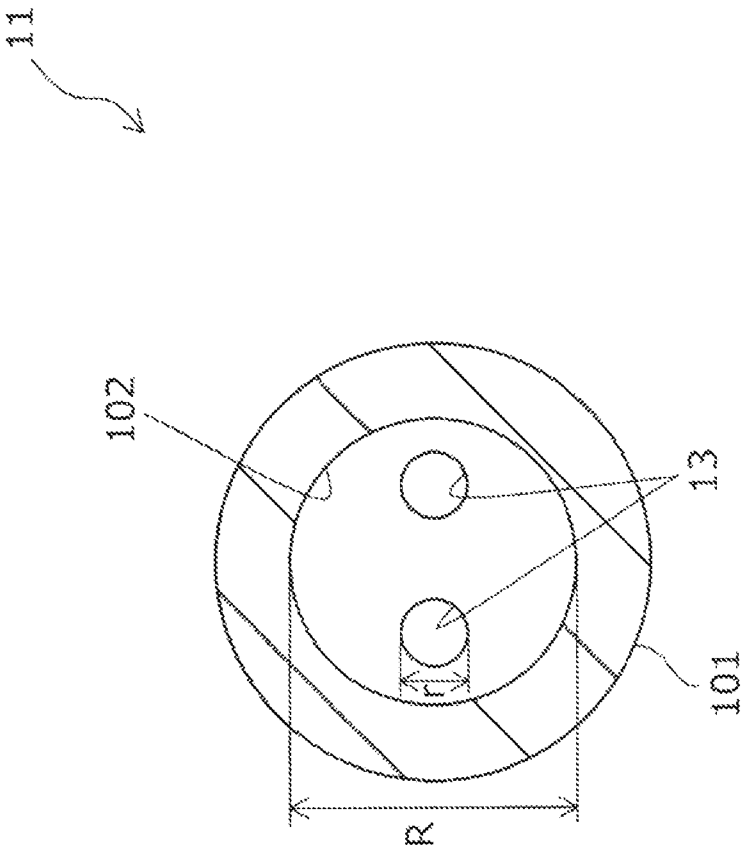
FIG. 8 is a schematic diagram of the jet nozzle when a plurality of (two) nozzle holes is formed.
Figure 9:
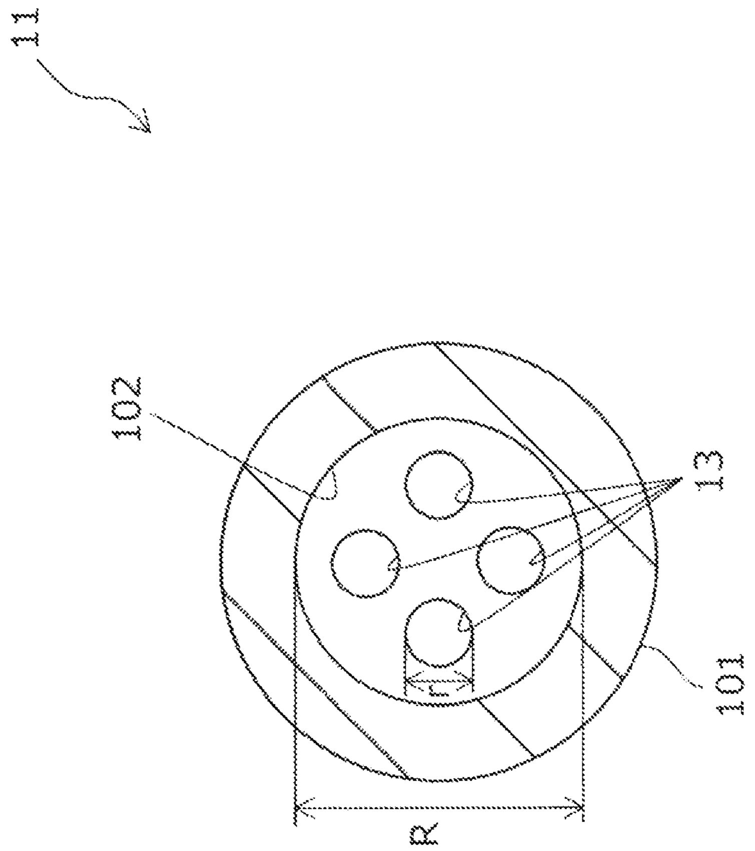
FIG. 9 is a schematic diagram of the jet nozzle when a plurality of (four) nozzle holes is formed.
Figure 10:
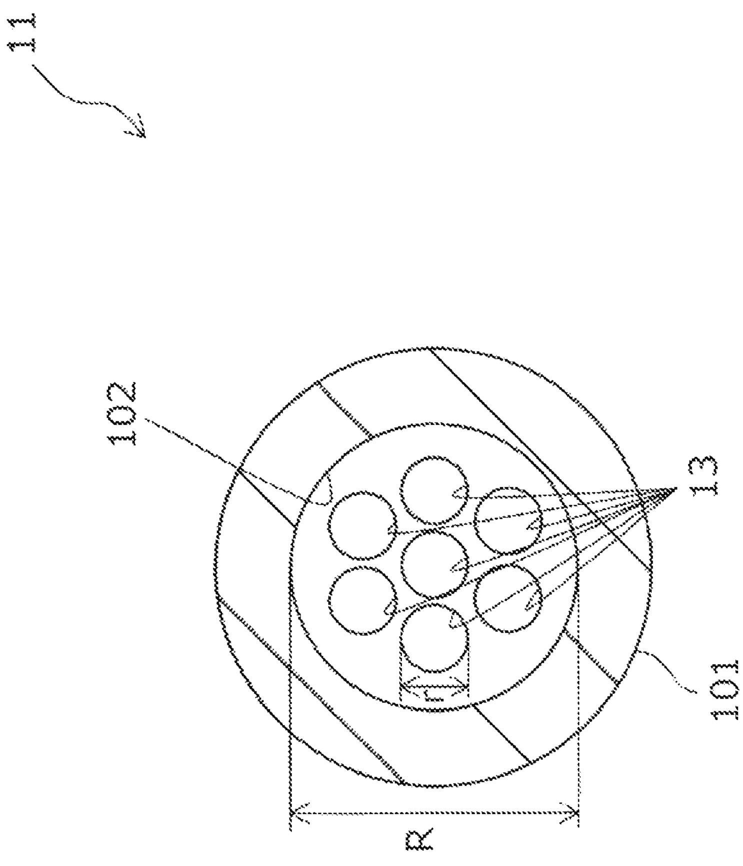
FIG. 10 is a schematic diagram of the jet nozzle when a plurality of (seven) nozzle holes is formed.

As long as Formula (65) is fulfilled, it is possible to design the flow channel 10 for the droplet jet device 25 to stably jet the droplets 7 having rectilinearity with an arbitrary shape just by deciding the nozzle hole diameter r and the number of the nozzle holes N. In another expression, by deciding the number of the nozzle holes N, the nozzle hole diameter r, and the contour length L of the cross-sectional surface of the flow channel so as to fulfill Formula (65) described above, and adopting the droplet jet device 25 decided in such a manner, it is possible to spray the liquid 3 in the state of the preferable droplets 7 irrespective of the cross-sectional shape of the flow channel 10. It should be noted that the contour length L of the cross-sectional surface of the flow channel means the contour length of the cross-sectional surface of the flow channel 10 in a portion adjacent to the jet nozzle 11. It should be noted that the number of the nozzle holes N is not particularly limited, and it is possible to adopt a variety of numbers as the number of the nozzle holes N as shown in FIG. 8 through FIG. 10.

$$3.13\times10^{2} < \frac{1}{N^2}\cdot\frac{\left(\frac{L}{\pi}\right)^2}{r^3} < 2.69\times10^{12} \tag{66}$$

$$3.13\times10^{2}\pi^2 < \frac{1}{N^2}\cdot\frac{L^2}{r^3} < 2.69\times10^{12}\pi^2$$

$$\therefore 3.09\times10^{3} < \frac{1}{N^2}\cdot\frac{L^2}{r^3} < 2.66\times10^{13}$$

Further, as long as Formula (66) is fulfilled, it is possible to design the flow channel 10 of the droplet jet device 25 capable of stably forming water and a variety of commercially available liquids 3 into droplets and jetting the droplets with an arbitrary shape just by deciding the nozzle hole diameter r and the number of the nozzle holes N. In another expression, by deciding the number of the nozzle holes N, the nozzle hole diameter r, and the contour length L of the cross-sectional surface of the flow channel so as to fulfill Formula (66) described above, and adopting the droplet jet device 25 decided in such a manner, it is possible to spray the liquid 3 in the state of the preferable droplets 7 irrespective of the cross-sectional shape of the flow channel 10 using almost all liquids 3 to be used generally.

$$2.81\times10^{7} < \frac{1}{N^2}\cdot\frac{\left(\frac{L}{\pi}\right)^2}{r^3} < 9.36\times10^{10} \tag{67}$$

$$2.81\times10^{7}\pi^2 < \frac{1}{N^2}\cdot\frac{L^2}{r^3} < 9.36\times10^{10}\pi^2$$

$$\therefore 2.77\times10^{8} < \frac{1}{N^2}\cdot\frac{L^2}{r^3} < 9.24\times10^{11}$$

Further, as long as Formula (67) is fulfilled, it is possible to design the flow channel 10 of the droplet jet device 25 capable of stably forming the water at the temperature no lower than 20 °C and no higher than 40 °C suitable for the skin cleaning into droplets and jetting the droplets with an arbitrary shape just by deciding the nozzle hole diameter r and the number of the nozzle holes N. In another expression, by deciding the number of the nozzle holes N, the nozzle hole diameter r, and the contour length L of the cross-sectional surface of the flow channel so as to fulfill Formula (67) described above, and adopting the droplet jet device 25 decided in such a manner, it is possible to spray the liquid 3 in the state of the preferable droplets 7 irrespective of the cross-sectional shape of the flow channel 10 using the water at the temperature no lower than 20 °C and no higher than 40 °C and the liquids 3 similar in characteristics to that water.

Here, Table 7 shows data obtained by adding the contour length L of the cross-sectional surface of the flow channel and values of $L^2/(N^2\cdot r^2)$ obtained using the contour length L to the data shown in Table 3.

TABLE 7

| LIQUID | VOLUME FLOW RATE Q ($m^3$/s) | FLOW CHANNEL CROSS-SECTIONAL AREA A ($m^2$) | KINEMATIC VISCOSITY COEFFICIENT ν ($m^2$/s) | JET VELOCITY v (m/s) | NUMBER OF NOZZLE JOLES N | Je |
|---|---|---|---|---|---|---|
| T | 8.33·E−08 | 7.85·E−07 | 2.18·E−05 | 47.0 | 1 | 73.76 |
| U | 8.33·E−08 | 3.32·E−05 | 9.78·E−07 | 24.0 | 7 | 5.02 |
| WATER | 3.50·E−08 | 3.32·E−05 | 1.00·E−06 | 22.7 | 7 | 2.72 |
| (20 °C) | 4.50·E−08 | 3.32·E−05 | 1.00·E−06 | 27.2 | 7 | 3.91 |
| | 5.33·E−08 | 3.32·E−05 | 1.00·E−06 | 34.0 | 7 | 6.12 |
| | 6.00·E−08 | 3.32·E−05 | 1.00·E−06 | 35.1 | 7 | 6.53 |
| | 6.67·E−08 | 3.32·E−05 | 1.00·E−06 | 41.9 | 7 | 9.30 |
| | 7.33·E−08 | 3.32·E−05 | 1.00·E−06 | 43.1 | 7 | 9.81 |
| | 8.00·E−08 | 3.32·E−05 | 1.00·E−06 | 49.9 | 7 | 13.16 |
| WATER | 3.50·E−08 | 3.32·E−05 | 8.00·E−07 | 21.5 | 7 | 2.51 |
| (30 °C) | 4.50·E−08 | 3.32·E−05 | 8.00·E−07 | 26.1 | 7 | 3.67 |
| | 5.33·E−08 | 3.32·E−05 | 8.00·E−07 | 31.7 | 7 | 5.45 |
| | 6.00·E−08 | 3.32·E−05 | 8.00·E−07 | 35.1 | 7 | 6.68 |
| | 6.67·E−08 | 3.32·E−05 | 8.00·E−07 | 41.9 | 7 | 9.51 |
| | 7.33·E−08 | 3.32·E−05 | 8.00·E−07 | 46.5 | 7 | 11.68 |
| | 8.00·E−08 | 3.32·E−05 | 8.00·E−07 | 49.9 | 7 | 13.45 |
| WATER | 3.50·E−08 | 3.32·E−05 | 6.58·E−07 | 21.5 | 7 | 2.56 |
| (40 °C) | 4.50·E−08 | 3.32·E−05 | 6.58·E−07 | 26.1 | 7 | 3.76 |
| | 5.33·E−08 | 3.32·E−05 | 6.58·E−07 | 35.1 | 7 | 6.83 |
| | 6.00·E−08 | 3.32·E−05 | 6.58·E−07 | 36.3 | 7 | 7.28 |
| | 6.67·E−08 | 3.32·E−05 | 6.58·E−07 | 43.1 | 7 | 10.26 |
| | 7.33·E−08 | 3.32·E−05 | 6.58·E−07 | 47.6 | 7 | 12.53 |
| | 8.00·E−08 | 3.32·E−05 | 6.58·E−07 | 51.0 | 7 | 14.39 |

TABLE 7-continued

| LIQUID | Re | FLOW CHANNEL DIAMETER R (m) | NOZZLE HOLE DIAMETER r (m) | FLOW CHANNEL CONTOUR LENGTH L (m) | $L^2/(N^2 \cdot r3)$ |
|---|---|---|---|---|---|
| T | 4.86 | 1.00·E−03 | 5.00·E−05 | 3.14·E−03 | 7.90·E+07 |
| U | 2.57 | 6.50·E−03 | 2.40·E−05 | 2.04·E−02 | 6.16·E+08 |
| WATER | 1.05 | 6.50·E−03 | 1.50·E−05 | 2.04·E−02 | 2.52·E+09 |
| (20 °C) | 1.35 | 6.50·E−03 | 1.50·E−05 | 2.04·E−02 | 2.52·E+09 |
| | 1.60 | 6.50·E−03 | 1.50·E−05 | 2.04·E−02 | 2.52·E+09 |
| | 1.80 | 6.50·E−03 | 1.50·E−05 | 2.04·E−02 | 2.52·E+09 |
| | 2.00 | 6.50·E−03 | 1.50·E−05 | 2.04·E−02 | 2.52·E+09 |
| | 2.20 | 6.50·E−03 | 1.50·E−05 | 2.04·E−02 | 2.52·E+09 |
| | 2.40 | 6.50·E−03 | 1.50·E−05 | 2.04·E−02 | 2.52·E+09 |
| WATER | 1.32 | 6.50·E−03 | 1.50·E−05 | 2.04·E−02 | 2.52·E+09 |
| (30 °C) | 1.69 | 6.50·E−03 | 1.50·E−05 | 2.04·E−02 | 2.52·E+09 |
| | 2.01 | 6.50·E−03 | 1.50·E−05 | 2.04·E−02 | 2.52·E+09 |
| | 2.26 | 6.50·E−03 | 1.50·E−05 | 2.04·E−02 | 2.52·E+09 |
| | 2.51 | 6.50·E−03 | 1.50·E−05 | 2.04·E−02 | 2.52·E+09 |
| | 2.76 | 6.50·E−03 | 1.50·E−05 | 2.04·E−02 | 2.52·E+09 |
| | 3.01 | 6.50·E−03 | 1.50·E−05 | 2.04·E−02 | 2.52·E+09 |
| WATER | 1.60 | 6.50·E−03 | 1.50·E−05 | 2.04·E−02 | 2.52·E+09 |
| (40 °C) | 2.06 | 6.50·E−03 | 1.50.5-05 | 2.04·E−02 | 2.52·E+09 |
| | 2.44 | 6.50·E−03 | 1.50·E−05 | 2.04·E−02 | 2.52·E+09 |
| | 2.75 | 6.50·E−03 | 1.50·E−05 | 2.04·E−02 | 2.52·E+09 |
| | 3.05 | 6.50·E−03 | 1.50·E−05 | 2.04·E−02 | 2.52·E+09 |
| | 3.36 | 6.50·E−03 | 1.50·E−05 | 2.04·E−02 | 2.52·E+09 |
| | 3.66 | 6.50·E−03 | 1.50·E−05 | 2.04·E−02 | 2.52·E+09 |

As shown in Table 7, it is understood that the values of $L^2/(N^2 \cdot r^2)$ are included in the ranges of Formula (65) and Formula (66) in all of the liquids. It is also understood that the values of $L^2/(N^2 \cdot r^2)$ in the water at the temperature no lower than 20 °C and no higher than 40 °C are all included in the range of Formula (67). In other words, it can be said that Formula (65) through Formula (67) appropriately represent the experimental values.

Regarding Cross-Sectional Area of Flow Channel

Then, there will be calculated the contour length L of the cross-sectional surface of the flow channel and the cross-sectional area Ac of the flow channel which are allowed in Formula (65) through Formula (67) when specifically setting the nozzle hole diameter r. The range of the contour length L of the cross-sectional surface of the flow channel can directly be decided based on Formula (65) through Formula (67). Further, when the range of the contour length L of the cross-sectional surface of the flow channel is decided, the maximum value of the cross-sectional area Ac of the flow channel corresponding to the range is also decided automatically. This uses the fact that when arbitrarily changing a shape of a figure while keeping the value of the contour length L of the cross-sectional surface constant, the area is maximized when the shape is a circular shape. In other words, the area of the circular shape corresponding to a maximum value Lmax of the contour length L of the cross-sectional surface of the flow channel takes a maximum value Acmax of the cross-sectional area Ac of the flow channel. When defining the maximum contour length of the flow channel as Lmax and a maximum diameter of a circular pipe having a circular cross-sectional shape as Rmax, $Lmax=\pi Rmax$ is true, and therefore, the maximum cross-sectional area Acmax of the flow channel is obtained as $Acmax=\pi Rmax^2/4=Lmax^2/4\pi$. Further, when the cross-sectional shape of the flow channel 10 is the rectangular shape, the cross-sectional area of the flow channel 10 is maximized when the cross-sectional shape is a square shape, and the maximum value is obtained as $Acrmax=Lmax^2/16$. A minimum contour length Lmin, the maximum contour length Lmax, a minimum diameter Rmin of the circular pipe having a circular shape corresponding to the minimum contour length Lmin, the maximum diameter Rmax of the circular pipe having a circular shape corresponding to the maximum contour length Lmax, the maximum cross-sectional area Acrmax of the flow channel when the cross-sectional shape is a rectangular shape, and the maximum cross-sectional area Acmax of the flow channel calculated based on Formula (65) through Formula (67) are respectively shown in Table 8 through Table 10.

TABLE 8

| NOZZLE HOLE DIAMETER r (μm) | MINIMUM CONTOUR LENGTH $L_{min}$ (m) | MAXIMUM CONTOUR LENGTH $L_{max}$ (m) | MINIMUN DIAMETER OF CIRCULAR PIPE $R_{min}$ (m) | MAXIMUM DIAMETER OF CIRCULAR PIPE $R_{max}$ (m) |
|---|---|---|---|---|
| 1 | 4.34E−10 × N | 1.26E−01 × N | 1.38E−10 × N | 4.00E−02 × N |
| 5 | 1.71E−09 × N | 4.97E−01 × N | 5.46E−10 × N | 1.58E−01 × N |
| 10 | 4.85E−09 × N | 1.41E+00 × N | 1.54E−09 × N | 4.47E−01 × N |
| 20 | 1.37E−08 × N | 3.97E+00 × N | 4.36E−09 × N | 1.27E+00 × N |
| 30 | 2.52E−08 × N | 7.30E+00 × N | 8.02E−09 × N | 2.32E+00 × N |
| 40 | 3.88E−08 × N | 1.12E+01 × N | 1.23E−08 × N | 3.58E+00 × N |
| 50 | 5.42E−08 × N | 1.57E+01 × N | 1.73E−08 × N | 5.00E+00 × N |
| 60 | 7.12E−08 × N | 2.07E+01 × N | 2.27E−08 × N | 6.57E+00 × N |
| 70 | 8.98E−08 × N | 2.60E+01 × N | 2.865−08 × N | 8.28E+00 × N |
| 80 | 1.10E−07 × N | 3.18E+01 × N | 3.49E−08 × N | 1.01E+01 × N |

TABLE 8-continued

| | | | | |
|---|---|---|---|---|
| 90 | 1.31E−07 × N | 3.79E+01 × N | 4.17E−08 × N | 1.21E+01 × N |
| 100 | 1.53E−07 × N | 4.44E+01 × N | 4.88E−08 × N | 1.41E+01 × N |
| 110 | 1.77E−07 × N | 5.13E+01 × N | 5.63E−08 × N | 1.63E+01 ×N |
| 120 | 2.02E−07 × N | 5.84E+01 × N | 6.41E−08 × N | 1.86E+01 × N |
| 130 | 2.27E−07 × N | 6.59E+01 × N | 7.23E−08 × N | 2.10E+01 × N |
| 140 | 2.54E−07 × N | 7.36E+01 × N | 8.08E−08 × N | 2.34E+01 × N |
| 150 | 2.82E−07 × N | 8.16E+01 × N | 8.96E−08 × N | 2.60E+01 × N |
| 160 | 3.10E−07 × N | 8.99E+01 × N | 9.88E−08 × N | 2.86E+01 × N |
| 170 | 3.40E−07 × N | 9.85E+01 × N | 1.08E−07 × N | 3.14E+01 × N |
| 180 | 3.70E−07 × N | 1.07E+02 × N | 1.18E−07 × N | 3.42E+01 × N |
| 190 | 4.01E−07 × N | 1.16E+02 × N | 1.28E−07 × N | 3.70E+01 × N |
| 200 | 4.34E−07 × N | 1.26E+02 × N | 1.38E−07 × N | 4.00E+01 × N |
| 300 | 7.97E−07 × N | 2.31E+02 × N | 2.54E−07 × N | 7.35E+01 × N |
| 400 | 1.23E−06 × N | 3.56E+02 × N | 3.90E−07 × N | 1.13E+02 × N |
| 500 | 1.71E−06 × N | 4.97E+02 × N | 5.46E−07 × N | 1.58E+02 × N |
| 600 | 2.25E−06 × N | 6.53E+02 × N | 7.17E−07 × N | 2.08E+02 × N |
| 700 | 2.84E−06 × N | 8.23E+02 × N | 9.04E−07 × N | 2.62E+02 × N |
| 800 | 3.47E−06 × N | 1.01E+03 × N | 1.10E−06 × N | 3.20E+02 × N |
| 900 | 4.14E−06 × N | 1.20E+03 × N | 1.32E−06 × N | 3.82E+02 × N |
| 1000 | 4.85E−06 × N | 1.41E+03 × N | 1.54E−06 × N | 4.47E+02 × N |

| NOZZLE HOLE DIAMETER r (μm) | MINIMUM CROSS-SECTIONAL AREA OF CIRCULAR PIPE $A_{c,min}$ ($m^2$) | MAXIMUM CROSS-SECTIONAL AREA OF RECTANGULAR FLOW CHANNEL $A_{c,max}$ ($m^2$) | MAXIMUM CROSS-SECTIONAL AREA OF FLOW CHANNEL $A_{c,max}$ ($m^2$) |
|---|---|---|---|
| 1 | 1.50E−20 × N^2 | 9.88E−04 × N^2 | 1.26E−03 × N^2 |
| 5 | 2.34E−19 × N^2 | 1.54E−02 × N^2 | 1.96E−02 × N^2 |
| 10 | 1.87E−18 × N^2 | 1.23E−01 × N^2 | 1.57E−01 × N^2 |
| 20 | 1.50E−17 × N^2 | 9.88E−01 × N^2 | 1.26E+00 × N^2 |
| 30 | 5.05E−17 × N^2 | 3.33E+00 × N^2 | 4.24E+00 × N^2 |
| 40 | 1.20E−16 × N^2 | 7.90E+00 × N^2 | 1.01E+01 × N^2 |
| 50 | 2.34E−16 × N^2 | 1.54E+01 × N^2 | 1.96E+01 × N^2 |
| 60 | 4.04E−16 × N^2 | 2.67E+01 × N^2 | 3.39E+01 × N^2 |
| 70 | 6.41E−16 × N^2 | 4.23E+01 × N^2 | 5.39E+01 × N^2 |
| 80 | 9.57E−16 × N^2 | 6.32E+01 × N^2 | 8.05E+01 × N^2 |
| 90 | 1.36E−15 × N^2 | 9.00E+01 × N^2 | 1.15E+02 × N^2 |
| 100 | 1.87E−15 × N^2 | 1.23E+02 × N^2 | 1.57E+02 × N^2 |
| 110 | 2.49E−15 × N^2 | 1.64E+02 × N^2 | 2.09E+02 × N^2 |
| 120 | 3.23E−15 × N^2 | 2.13E+02 × N^2 | 2.72E+02 × N^2 |
| 130 | 4.11E−15 × N^2 | 2.11E+02 × N^2 | 3.45E+02 × N^2 |
| 140 | 5.13E−15 × N^2 | 3.39E+02 × N^2 | 4.31E+02 × N^2 |
| 150 | 6.31E−15 × N^2 | 4.17E+02 × N^2 | 5.30E+02 × N^2 |
| 160 | 7.66E−15 × N^2 | 5.06E+02 × N^2 | 6.44E+02 × N^2 |
| 170 | 9.19E−15 × N^2 | 6.06E+02 × N^2 | 7.72E+02 × N^2 |
| 180 | 1.09E−14 × N^2 | 7.20E+02 × N^2 | 9.17E+02 × N^2 |
| 190 | 1.28E−14 × N^2 | 8.47E+02 × N^2 | 1.08E+03 × N^2 |
| 200 | 1.50E−14 × N^2 | 9.88E+02 × N^2 | 1.26E+03 × N^2 |
| 300 | 5.05E−14 × N^2 | 3.33E+03 × N^2 | 4.24E+03 × N^2 |
| 400 | 1.20E−13 × N^2 | 7.90E+03 × N^2 | 1.01E+04 × N^2 |
| 500 | 2.34E−13 × N^2 | 1.54E+04 × N^2 | 1.96E+04 × N^2 |
| 600 | 4.04E−13 × N^2 | 2.67E+04 × N^2 | 3.39E+04 × N^2 |
| 700 | 6.41E−13 × N^2 | 4.23E+04 × N^2 | 5.39E+04 × N^2 |
| 800 | 9.57E−13 × N^2 | 6.32E+04 × N^2 | 8.05E+04 × N^2 |
| 900 | 1.36E−12 × N^2 | 9.00E+04 × N^2 | 1.15E+05 × N^2 |
| 1000 | 1.87E−12 × N^2 | 1.23E+05 × N^2 | 1.57E+05 × N^2 |

TABLE 9

| NOZZLE HOLE DIAMETER r (μm) | MINIMUM CONTOUR LENGTH $L_{min}$ (m) | MAXIMUM CONTOUR LENGTH $L_{max}$ (m) | MINIMUN DIAMETER OF CIRCULAR PIPE $R_{min}$ (m) | MAXIMUM DIAMETER OF CIRCULAR PIPE $R_{max}$ (m) |
|---|---|---|---|---|
| 1 | 5.56E−08 × N | 5.16E−03 × N | 1.77E−08 × N | 1.64E−03 × N |
| 5 | 2.20E−07 × N | 2.04E−02 × N | 6.99E−08 × N | 6.49E−03 × N |
| 10 | 6.21E−07 × N | 5.77E−02 × N | 1.98E−07 × N | 1.84E−02 × N |
| 20 | 1.76E−06 × N | 1.63E−01 × N | 5.60E−07 × N | 5.19E−02 × N |
| 30 | 3.23E−06 × N | 3.00E−01 × N | 1.03E−06 × N | 9.54E−02 × N |
| 10 | 4.97E−06 × N | 4.61E−01 × N | 1.58E−06 × N | 1.47E−01 × N |
| 50 | 6.95E−06 × N | 6.45E−01 × N | 2.21E−06 × N | 2.05E−01 × N |
| 60 | 9.13E−06 × N | 8.47E−01 × N | 2.91E−05 × N | 2.70E−01 × N |
| 70 | 1.15E−05 × N | 1.07E+00 × N | 3.66E−05 × N | 3.40E−01 × N |
| 80 | 3.41E−05 × N | 1.30E+00 × N | 4.48E−06 × N | 4.15E−01 × N |
| 90 | 1.68E−05 × N | 1.56E+00 × N | 5.34E−06 × N | 4.96E−01 × N |
| 100 | 1.97E−05 × N | 1.82E+00 × N | 6.26E−05 × N | 5.80E−01 × N |

TABLE 9-continued

| | | | | |
|---|---|---|---|---|
| 110 | 2.27E−05 × N | 2.10E+00 × N | 7.22E−05 × N | 6.70E−01 × N |
| 120 | 2.58E−05 × N | 2.40E+00 × N | 3.22E−05 × N | 7.63E−01 × N |
| 130 | 2.91E−05 × N | 2.70E+00 × N | 9.27E−05 × N | 8.60E−01 × N |
| 140 | 3.26E−05 × N | 3.02E+00 × N | 1.04E−05 × N | 9.61E−01 × N |
| 150 | 3.61E−05 × N | 3.35E+00 × N | 1.15E−05 × N | 1.07E+00 × N |
| 160 | 3.98E−05 × N | 3.69E+00 × N | 1.27E−05 × N | 1.17E+00 × N |
| 170 | 4.36E−05 × N | 4.04E+00 × N | 1.39E−05 × N | 1.29E+00 × N |
| 180 | 4.75E−05 × N | 4.40E+00 × N | 1.51E−05 × N | 1.40E+00 × N |
| 190 | 5.15E−05 × N | 4.78E+00 × N | 1.64E−05 × N | 1.52E+00 × N |
| 200 | 5.56E−05 × N | 5.16E+00 × N | 1.77E−05 × N | 1.64E+00 × N |
| 300 | 1.02E−04 × N | 9.47E+00 × N | 3.25E−05 × N | 3.02E+00 × N |
| 400 | 1.57E−04 × N | 1.46E+01 × N | 5.00E−05 × N | 4.64E+00 × N |
| 500 | 2.20E−04 × N | 2.04E+01 × N | 6.99E−05 × N | 6.49E+00 × N |
| 600 | 2.89E−04 × N | 2.68E+01 × N | 9.19E−05 × N | 8.53E+00 × N |
| 700 | 3.64E−04 × N | 3.38E+01 × N | 1.16E−04 × N | 1.07E+01 × N |
| 800 | 4.45E−04 × N | 4.13E+01 × N | 1.42E−04 × N | 1.31E+01 × N |
| 900 | 5.31E−04 × N | 4.92E+01 × N | 1.69E−04 × N | 1.57E+01 × N |
| 1000 | 6.21E−04 × N | 5.77E+01 × N | 1.98E−04 × N | 1.84E+01 × N |

| NOZZLE HOLE DIAMETER r (μm) | MINIMUM CROSS-SECTIONAL AREA OF CIRCULAR PIPE $A_{c,min}$ ($m^2$) | MAXIMUM CROSS-SECTIONAL AREA OF RECTANGULAR FLOW CHANNEL $A_{c,max}$ ($m^2$) | MAXIMUM CROSS-SECTIONAL AREA OF FLOW CHANNEL $A_{c,max}$ ($m^2$) |
|---|---|---|---|
| 1 | 2.46E−16 × N^2 | 1.93E−16 × N^2 | 1.66E−06 × N^2 |
| 5 | 3.84E−15 × N^2 | 3.02E−15 × N^2 | 2.60E−05 × N^2 |
| 10 | 3.07E−14 × N^2 | 2.41E−14 × N^2 | 2.08E−04 × N^2 |
| 20 | 2.46E−13 × N^2 | 1.93E−13 × N^2 | 1.56E−03 × N^2 |
| 30 | 8.30E−13 × N^2 | 6.52E−13 × N^2 | 5.61E−03 × N^2 |
| 10 | 1.97E−12 × N^2 | 1.55E−12 × N^2 | 1.33E−02 × N^2 |
| 50 | 3.84E−12 × N^2 | 3.02E−12 × N^2 | 2.60E−02 × N^2 |
| 60 | 6.64E−12 × N^2 | 5.21E−12 × N^2 | 4.49E−02 × N^2 |
| 70 | 1.05E−11 × N^2 | 828E−12 × N^2 | 7.13E−02 × N^2 |
| 80 | 1.57E−11 × N^2 | 1.24E−11 × N^2 | 1.06E−01 × N^2 |
| 90 | 2.24E−11 × N^2 | 1.76E−11 × N^2 | 1.51E−01 × N^2 |
| 100 | 3.07E−11 × N^2 | 2.41E−11 × N^2 | 2.08E−01 × N^2 |
| 110 | 4.09E−11 × N^2 | 3.21E−11 × N^2 | 2.77E−01 × N^2 |
| 120 | 5.31E−11 × N^2 | 4.17E−11 × N^2 | 3.59E−01 × N^2 |
| 130 | 6.75E−11 × N^2 | 5.30E−11 × N^2 | 4.57E−01 × N^2 |
| 140 | 8.43E−11 × N^2 | 6.62E−11 × N^2 | 5.70E−01 × N^2 |
| 150 | 1.04E−10 × N^2 | 8.15E−11 × N^2 | 7.01E−01 × N^2 |
| 160 | 1.26E−10 × N^2 | 9.89E−11 × N^2 | 8.51E−01 × N^2 |
| 170 | 1.51E−10 × N^2 | 1.19E−10 × N^2 | 1.02E+00 × N^2 |
| 180 | 1.79E−10 × N^2 | 1.41E−10 × N^2 | 1.21E+00 × N^2 |
| 190 | 2.11E−10 × N^2 | 1.66E−10 × N^2 | 1.43E+00 × N^2 |
| 200 | 2.46E−10 × N^2 | 1.93E−10 × N^2 | 1.66E+00 × N^2 |
| 300 | 8.30E−10 × N^2 | 6.52E−10 × N^2 | 5.61E+00 × N^2 |
| 400 | 1.97E−09 × N^2 | 1.55E−09 × N^2 | 1.33E+01 × N^2 |
| 500 | 3.84E−09 × N^2 | 3.02E−09 × N^2 | 2.60E+01 × N^2 |
| 600 | 6.64E−09 × N^2 | 5.21E−09 × N^2 | 4.49E+01 × N^2 |
| 700 | 1.05E−08 × N^2 | 8.28E−09 × N^2 | 7.13E+01 × N^2 |
| 800 | 1.57E−08 × N^2 | 1.24E−08 × N^2 | 1.06E+02 × N^2 |
| 900 | 2.24E−08 × N^2 | 1.76E−08 × N^2 | 1.51E+02 × N^2 |
| 1000 | 3.07E−08 × N^2 | 2.41E−08 × N^2 | 2.08E+02 × N^2 |

TABLE 10

| NOZZLE HOLE DIAMETER r (μm) | MINIMUM CONTOUR LENGTH $L_{min}$ (m) | MAXIMUM CONTOUR LENGTH $L_{max}$ (m) | MINIMUN DIAMETER OF CIRCULAR PIPE $R_{min}$ (m) | MAXIMUM DIAMETER OF CIRCULAR PIPE $R_{max}$ (m) |
|---|---|---|---|---|
| 1 | 1.66E−05 × N | 9.61E−04 × N | 5.30E−06 × N | 3.06E−04 × N |
| 5 | 6.58E−05 × N | 3.80E−03 × N | 2.09E−05 × N | 1.21E−03 × N |
| 10 | 1.86E−04 × N | 1.07E−02 × N | 5.92E−05 × N | 3.42E−03 × N |
| 20 | 5.26E−04 × N | 3.04E−02 × N | 1.68E−04 × N | 9.68E−03 × N |
| 30 | 9.67E−04 × N | 5.58E−02 × N | 3.08E−04 × N | 1.78E−07 × N |
| 40 | 1.49E−03 × N | 8.60E−02 × N | 4.74E−04 × N | 2.74E−02 × N |
| 50 | 2.08E−03 × N | 1.20E−01 × N | 6.62E−04 × N | 3.82E−02 × N |
| 60 | 2.73E−03 × N | 1.58E−01 × N | 8.71E−04 × N | 5.03E−02 × N |
| 70 | 3.45E−03 × N | 1.99E−01 × N | 1.10E−03 × N | 6.34E−02 × N |
| 80 | 4.21E−03 × N | 2.43E−01 × N | 1.34E−03 × N | 7.74E−02 × N |
| 90 | 5.02E−03 × N | 2.90E−01 × N | 1.60E−03 × N | 9.24E−02 × N |
| 100 | 5.88E−03 × N | 3.40E−01 × N | 1.87E−03 × N | 1.08E−01 × N |
| 110 | 6.79E−03 × N | 3.92E−01 × N | 2.16E−03 × N | 1.25E−01 × N |
| 120 | 7.74E−03 × N | 4.47E−01 × N | 2.46E−03 × N | 1.42E−01 × N |

TABLE 10-continued

| | | | | |
|---|---|---|---|---|
| 130 | 8.72E−03 × N | 5.04E−01 × N | 2.78E−03 × N | 1.60E−01 × N |
| 140 | 9.75E−03 × N | 5.63E−01 × N | 3.10E−03 × N | 1.79E−01 × N |
| 150 | 1.08E−02 × N | 6.24E−01 × N | 3.44E−03 × N | 1.99E−01 × N |
| 160 | 1.19E−02 × N | 6.88E−01 × N | 3.79E−03 × N | 2.19E−01 × N |
| 170 | 1.30E−02 × N | 7.53E−01 × N | 4.15E−03 × N | 2.40E−01 × N |
| 180 | 1.42E−02 × N | B.21E−01 × N | 4.52E−03 × N | 2.61E−01 × N |
| 190 | 1.54E−02 × N | 8.90E−01 × N | 4.91E−03 × N | 2.83E−01 × N |
| 200 | 1.66E−02 × N | 9.61E−01 × N | 5.30E−03 × N | 3.06E−01 × N |
| 300 | 3.06E−02 × N | 1.77E+00 × N | 9.73E−03 × N | 5.62E−01 × N |
| 400 | 4.71E−02 × N | 2.72E+00 × N | 1.50E−02 × N | 8.65E−01 × N |
| 500 | 6.58E−02 × N | 3.80E+00 × N | 2.09E−02 × N | 1.21E+00 × N |
| 600 | 8.65E−02 × N | 4.99E+00 × N | 2.75E−02 × N | 1.59E+00 × N |
| 700 | 1.09E−01 × N | 6.29E+00 × N | 3.47E−02 × N | 2.00E+00 × N |
| 800 | 1.33E−01 × N | 7.69E+00 × N | 4.24E−02 × N | 2.45E+00 × N |
| 900 | 1.59E−01 × N | 9.18E+00 × N | 5.06E−02 × N | 2.92E+00 × N |
| 1000 | 1.86E−01 × N | 1.07E+01 × N | 5.92E−02 × N | 3.42E+00 × N |

| NOZZLE HOLE DIAMETER r (μm) | MINIMUM CROSS-SECTIONAL AREA OF CIRCULAR PIPE $A_{c,min}$ (m$^2$) | MAXIMUM CROSS-SECTIONAL AREA OF RECTANGULAR FLOW CHANNEL $A_{c,max}$ (m$^2$) | MAXIMUM CROSS-SECTIONAL AREA OF FLOW CHANNEL $A_{c,max}$ (m$^2$) |
|---|---|---|---|
| 1 | 2.20E−11 × N^2 | 5.78E−08 × N^2 | 7.35E−08 × N^2 |
| 5 | 3.44E−10 × N^2 | 9.02E−07 × N^2 | 1.15E−06 × N^2 |
| 10 | 2.76E−09 × N^2 | 7.22E−06 × N^2 | 9.19E−06 × N^2 |
| 20 | 2.20E−08 × N^2 | 5.78E−05 × N^2 | 7.35E−05 × N^2 |
| 30 | 7.44E−08 × N^2 | 1.95E−04 × N^2 | 2.48E−04 × N^2 |
| 40 | 1.76E−07 × N^2 | 4.62E−04 × N^2 | 5.88E−04 × N^2 |
| 50 | 3.44E−07 × N^2 | 9.02E−04 × N^2 | 1.15E−03 × N^2 |
| 60 | 5.95E−01 × N^2 | 1.56E−03 × N^2 | 1.99E−03 × N^2 |
| 70 | 9.45E−07 × N^2 | 2.48E−03 × N^2 | 3.15E−03 × N^2 |
| 80 | 1.41E−06 × N^2 | 3.70E−03 × N^2 | 4.71E−03 × N^2 |
| 90 | 2.01E−06 × N^2 | 5.26E−03 × N^2 | 6.70E−03 × N^2 |
| 100 | 2.76E−06 × N^2 | 7.22E−03 × N^2 | 9.19E−03 × N^2 |
| 110 | 3.67E−06 × N^2 | 9.61E−03 × N^2 | 1.22E−02 × N^2 |
| 120 | 4.76E−06 × N^2 | 1.25E−02 × N^2 | 1.59E−02 × N^2 |
| 130 | 6.05E−06 × N^2 | 1.590-02 × N^2 | 2.02E−02 × N^2 |
| 140 | 7.55E−06 × N^2 | 1.98E−02 × N^2 | 2.52E−02 × N^2 |
| 150 | 9.30E−06 × N^2 | 2.44E−02 × N^2 | 3.10E−02 × N^2 |
| 160 | 1.13E−05 × N^2 | 2.96E−02 × N^2 | 3.76E−02 × N^2 |
| 170 | 1.35E−05 × N^2 | 3.55E−02 × N^2 | 4.52E−02 × N^2 |
| 180 | 1.61E−05 × N^2 | 4.21E−02 × N^2 | 5.36E−02 × N^2 |
| 190 | 1.89E−05 × N^2 | 4.95E−02 × N^2 | 6.30E−02 × N^2 |
| 200 | 2.20E−05 × N^2 | 5.78E−02 × N^2 | 7.35E−02 × N^2 |
| 300 | 7.44E−05 × N^2 | 1.95E−01 × N^2 | 2.48E−01 × N^2 |
| 400 | 1.76E−04 × N^2 | 4.62E−01 × N^2 | 5.88E−01 × N^2 |
| 500 | 3.44E−04 × N^2 | 9.02E−01 × N^2 | 1.15E+00 × N^2 |
| 600 | 5.95E−04 × N^2 | 1.56E +00 × N^2 | 1.99E+00 × N^2 |
| 700 | 9.45E−04 × N^2 | 2.48E+00 × N^2 | 3.15E+00 × N^2 |
| 800 | 1.41E−03 × N^2 | 3.70E +00 × N^2 | 4.71E+00 × N^2 |
| 900 | 2.01E−03 × N^2 | 5.26E +00 × N^2 | 6.70E+00 × N^2 |
| 1000 | 2.76E−03 × N^2 | 7.22E +00 × N^2 | 9.19E+00 × N^2 |

When Nozzle Hole Diameter is No Smaller than 100 μm and No Larger than 1 mm

When defining the number of the nozzle holes as N, the contour length of the cross-sectional surface of the flow channel as L [m], and the cross-sectional area of the flow channel as Ac [m$^2$], by making L fall within the range of Formula (68) described below, it is possible to form almost all liquids 3 into the droplets to jet the droplets, and therefore, the droplet jet device 25 having the flow channel 10 and the nozzle hole 13 can be used as the cleaning equipment using the impact power by the liquid 3 formed into the droplets. In another expression, by adopting such a configuration as to fulfill Formula (68) as described above, when the diameter r of the nozzle hole is in a range no smaller than 100 μm and no larger than 1 mm, it is possible to spray the liquid 3 in the state of the preferable droplets 7 irrespective of the cross-sectional shape of the flow channel 10 using almost all liquids 3 to be used generally.

$$1.53\times10^{-7}N<L<1.41\times10^{3}N \quad (68)$$

Further, by making L fall within the range of Formula (69) described below obtained from Table 9, since it is possible to form almost all liquids 3 easily available for an ordinary person into the droplets to jet the droplets, the droplet jet device having the flow channel 10 and the nozzle hole 13 can be used as the cleaning equipment which uses the impact power by the liquid 3 formed into the droplets, which is suitable for general purposes, and which has portability. In another expression, by adopting such a configuration as to fulfill Formula (69) as described above, when the diameter r of the nozzle hole is in the range no smaller than 100 μm and no larger than 1 mm, it is possible to spray the liquid 3 in the state of the preferable droplets 7 irrespective of the cross-sectional shape of the flow channel 10 using almost all liquids 3 to be used generally in the cleaning equipment, the cosmetic equipment, and so on.

$$1.97\times10^{-5}N<L<5.77\times10^{1}N \quad (69)$$

Further, by designing the flow channel 10 and the nozzle hole 13 so as to make L fall within the range of Formula (70)

obtained from Table 10, it is possible to form the water at the temperature no lower than 20 °C and no higher than 40 °C into the droplets to jet the droplets, and therefore, the droplet jet device 25 having the flow channel 10 and the nozzle hole 13 can be used as the cleaning equipment using the impact power by the water thus formed into the droplets. In another expression, by adopting such a configuration as to fulfill Formula (70) as described above, when the diameter r of the nozzle hole is in the range no smaller than 100 μm and no larger than 1 mm, it is possible to spray the liquid 3 in the state of the preferable droplets 7 irrespective of the cross-sectional shape of the flow channel 10 using the water at the temperature no lower than 20 °C and no higher than 40 °C and the liquids 3 similar in characteristics to that water.

$$5.88\times10^{-3}N<L<1.07\times10^{1}N \quad (70)$$

Further, by designing the flow channel 10 and the nozzle hole 13 so as to make Ac fulfill Formula (71) obtained from Table 10, it is possible to form the water at the temperature no lower than 20 °C and no higher than 40 °C into the droplets to jet the droplets, and therefore, the droplet jet device 25 having the flow channel 10 and the nozzle hole 13 can be used as the cleaning equipment using the impact power by the water thus formed into the droplets. In another expression, by adopting such a configuration as to fulfill Formula (71) as described above, when the diameter r of the nozzle hole is in the range no smaller than 100 μm and no larger than 1 mm, it is possible to spray the liquid 3 in the state of the preferable droplets 7 irrespective of the cross-sectional shape of the flow channel 10 using the water at the temperature no lower than 20 °C and no higher than 40 °C and the liquids 3 similar in characteristics to that water.

$$2.76\times10^{-6}N^2<A_c<9.19N^2 \quad (71)$$

When Nozzle Hole Diameter is No Smaller than 1 μm and No Larger than 100 μm

When defining the number of the nozzle holes as N, the contour length of the cross-sectional surface of the flow channel as L [m], and the cross-sectional area of the flow channel as Ac [m$^2$], by making L fall within the range of Formula (72) described below, it is possible to form almost all liquids 3 into the droplets to jet the droplets, and therefore, the droplet jet device 25 having the flow channel 10 and the nozzle hole 13 can be used as the cleaning equipment using the impact power by the liquid 3 formed into the droplets. In another expression, by adopting such a configuration as to fulfill Formula (72) as described above, when the diameter r of the nozzle hole is in a range no smaller than 1 μm and no larger than 100 μm, it is possible to spray the liquid 3 in the state of the preferable droplets 7 irrespective of the cross-sectional shape of the flow channel 10 using almost all liquids 3 to be used generally.

$$4.34\times10^{-10}N<L<4.44\times10^{1}N \quad (72)$$

Further, by making L fall within the range of Formula (73) described below obtained from Table 9, since it is possible to form almost all liquids 3 easily available for an ordinary person into the droplets to jet the droplets, the droplet jet device having the flow channel 10 and the nozzle hole 13 can be used as the cleaning equipment which uses the impact power by the liquid 3 formed into the droplets, which is suitable for general purposes, and which has portability. In another expression, by adopting such a configuration as to fulfill Formula (73) as described above, when the diameter r of the nozzle hole is in the range no smaller than 1 μm and no larger than 100 μm, it is possible to spray the liquid 3 in the state of the preferable droplets 7 irrespective of the cross-sectional shape of the flow channel 10 using almost all liquids 3 to be used generally in the cleaning equipment, the cosmetic equipment, and so on.

$$5.56\times10^{-8}N<L<1.82N \quad (73)$$

Further, by designing the flow channel 10 and the nozzle hole 13 so as to make L fall within the range of Formula (74) obtained from Table 10, it is possible to form the water at the temperature no lower than 20 °C and no higher than 40 °C into the droplets to jet the droplets, and therefore, the droplet jet device 25 having the flow channel 10 and the nozzle hole 13 can be used as the cleaning equipment using the impact power by the water thus formed into the droplets. In another expression, by adopting such a configuration as to fulfill Formula (74) as described above, when the diameter r of the nozzle hole is in the range no smaller than 1 μm and no larger than 100 μm, it is possible to spray the liquid 3 in the state of the preferable droplets 7 irrespective of the cross-sectional shape of the flow channel 10 using the water at the temperature no lower than 20 °C and no higher than 40 °C and the liquids 3 similar in characteristics to that water.

$$1.66\times10^{-5}N<L<3.40\times10^{-1}N \quad (74)$$

Further, by designing the flow channel 10 and the nozzle hole 13 so as to make Ac fulfill Formula (75) obtained from Table 10, it is possible to form the water at the temperature no lower than 20 °C and no higher than 40 °C into the droplets to jet the droplets, and therefore, the droplet jet device 25 having the flow channel 10 and the nozzle hole 13 can be used as the cleaning equipment using the impact power by the water thus formed into the droplets. In another expression, by adopting such a configuration as to fulfill Formula (75) as described above, when the diameter r of the nozzle hole is in the range no smaller than 1 μm and no larger than 100 μm, it is possible to spray the liquid 3 in the state of the preferable droplets 7 irrespective of the cross-sectional shape of the flow channel 10 using the water at the temperature no lower than 20 °C and no higher than 40 °C and the liquids 3 similar in characteristics to that water.

$$2.20\times10^{-11}N^2<A_c<9.19\times10^{-3}N^2 \quad (75)$$

On the other hand, by designing the flow channel 10 and the nozzle hole 13 so as to fulfill Formula (76) described below based on Table 10, when the cross-sectional shape of the flow channel is the circular shape, and the diameter r of the nozzle hole is in the range no smaller than 1 μm and no larger than 100 μm, it is possible to spray the liquid 3 in the state of the preferable droplets 7 using almost all liquids 3 to be used generally.

$$5.30\times10^{-6}N<R<1.08\times10^{-1}N \quad (76)$$

Further, by designing the flow channel 10 and the nozzle hole 13 so as to fulfill Formula (77) described below based on Table 10, when the cross-sectional shape of the flow channel 10 is the rectangular shape, and the diameter r of the nozzle hole is in the range no smaller than 1 μm and no larger than 100 μm, it is possible to spray the liquid 3 in the state of the preferable droplets 7 using the water at the temperature no lower than 20 °C and no higher than 40 °C and the liquids 3 similar in characteristics to that water. Alternatively, when the cross-sectional shape of the flow channel 10 is a square shape, and the diameter r of the nozzle hole is in the range no smaller than 1 μm and no larger than 100 μm, it is possible to spray the liquid 3 in the state of the preferable droplets 7.

$$2.20\times10^{-11}N^2<A_c<7.22\times10^{-3}N^2 \quad (77)$$

What is claimed is:

1. A droplet jet device configured to form a liquid into droplets to jet the droplets, the droplet jet device comprising:

a jet nozzle having at least one nozzle hole and spraying the liquid from the nozzle hole in a continuous flow state;

a pressurizing liquid supplier having a flow channel through which the liquid in a laminar flow state circulates and pressurizing the liquid in the flow channel to feed the liquid to the jet nozzle; and a controller configured to control an operation of the pressurizing liquid supplier to make the liquid sprayed from the nozzle hole in a state of being fragmented into droplets from the continuous flow, wherein the jet nozzle and the flow channel have dimensions such that $$0.188 < \frac{1}{N^2} \cdot \frac{L^2}{r^3} \leq 3.19 \times 10^7,$$

where N is a number of the nozzle holes, r [m] is a diameter of the nozzle hole, and L [m] is a contour length of a boundary of a cross section of the flow channel, and the diameter of the nozzle hole is in a range of 1 μm to 90 μm.

2. The droplet jet device according to claim 1, wherein $$3.09 \times 10^3 < \frac{1}{N^2} \cdot \frac{L^2}{r^3} \leq 3.19 \times 10^7.$$

3. A droplet jet device configured to form a liquid into droplets to jet the droplets, the droplet jet device comprising:

a jet nozzle having at least one nozzle hole and spraying the liquid from the nozzle hole in a continuous flow state;

a pressurizing liquid supplier having a flow channel through which the liquid circulates and pressurizing the liquid in the flow channel to feed the liquid to the jet nozzle; and a controller configured to control an operation of the pressurizing liquid supplier to make the liquid sprayed from the nozzle hole in a state of being fragmented into droplets from the continuous flow, wherein the flow channel has a circular cross-sectional shape, the jet nozzle and the flow channel have dimensions such that $$1.90 \times 10^{-2} < \frac{1}{N^2} \cdot \frac{R^2}{r^3} < 8.10 \times 10^5,$$

where N is a number of the nozzle holes, r [m] is a diameter of the nozzle hole, and R [m] is a diameter of the flow channel, and the diameter of the nozzle hole is in a range of 1 μm to 90 μm.

4. The droplet jet device according to claim 3, wherein $$3.13 \times 10^2 < \frac{1}{N^2} \cdot \frac{R^2}{r^3} < 8.10 \times 10^5.$$

5. A droplet jet device configured to form a liquid into droplets to jet the droplets, the droplet jet device comprising:

a jet nozzle having at least one nozzle hole and spraying the liquid from the nozzle hole in a continuous flow state;

a pressurizing liquid supplier having a flow channel through which the liquid circulates and pressurizing the liquid in the flow channel to feed the liquid to the jet nozzle; and a controller configured to control an operation of the pressurizing liquid supplier to make the liquid sprayed from the nozzle hole in a state of being fragmented into droplets from the continuous flow, wherein the flow channel has a rectangular cross-sectional shape, the jet nozzle and the flow channel have dimensions such that $$4.69 \times 10^{-2} < \frac{1}{N^2} \cdot \frac{(a+b)^2}{r^3} < 1.62 \times 10^6,$$

where N is a number of the nozzle holes, r [m] is a diameter of the nozzle hole, a [m] is a length of a first side of the cross-sectional shape of the flow channel, and b [m] is a length of a second side of the cross-sectional shape of the flow channel which intersects with the first side, and the diameter of the nozzle hole is in a range of 1 μm to 90 μm.

6. The droplet jet device according to claim 5, wherein $$7.73 \times 10^2 < \frac{1}{N^2} \cdot \frac{(a+b)^2}{r^3} < 1.62 \times 10^6.$$

* * * * *